(12) United States Patent
Tetzner et al.

(10) Patent No.: US 8,771,939 B2
(45) Date of Patent: Jul. 8, 2014

(54) METHOD FOR METHYLATION ANALYSIS OF NUCLEIC ACID

(75) Inventors: Reimo Tetzner, Berlin (DE); Joern Lewin, Berlin (DE)

(73) Assignee: Epigenomics AG, Berlin (DE)

( * ) Notice: Subject to any disclaimer, the term of this patent is extended or adjusted under 35 U.S.C. 154(b) by 552 days.

(21) Appl. No.: 12/310,051

(22) PCT Filed: Aug. 1, 2007

(86) PCT No.: PCT/EP2007/006810
§ 371 (c)(1),
(2), (4) Date: Feb. 9, 2009

(87) PCT Pub. No.: WO2008/017411
PCT Pub. Date: Feb. 14, 2008

(65) Prior Publication Data
US 2010/0092951 A1  Apr. 15, 2010

(30) Foreign Application Priority Data
Aug. 8, 2006 (EP) .................................... 06090132

(51) Int. Cl.
*C12Q 1/68* (2006.01)
*C12P 19/34* (2006.01)
*C07H 21/02* (2006.01)
*C07H 21/04* (2006.01)

(52) U.S. Cl.
USPC .......... 435/6.1; 435/91.1; 435/91.2; 536/24.3

(58) Field of Classification Search
None
See application file for complete search history.

(56) References Cited

U.S. PATENT DOCUMENTS

| | | | |
|---|---|---|---|
| 6,214,556 B1 * | 4/2001 | Olek et al. | 435/6 |
| 6,524,613 B1 * | 2/2003 | Steer et al. | 424/450 |
| 7,846,693 B2 * | 12/2010 | Millar et al. | 435/91.2 |
| 2006/0234317 A1 * | 10/2006 | O'Donnell et al. | 435/7.22 |

FOREIGN PATENT DOCUMENTS

| | | | |
|---|---|---|---|
| AU | WO 03/006932 | * | 8/2003 |
| AU | WO 2005/024053 | * | 3/2005 |
| EP | 1 584 629 A1 | | 10/2005 |
| WO | WO 00/43531 A2 | | 7/2000 |
| WO | WO 00/70090 | * | 11/2000 |
| WO | WO 2005/098035 A2 | | 10/2005 |

OTHER PUBLICATIONS

Laird; Nature Reviews, vol. 3, Apr. 2003, pp. 253-266.*
Quayle et al., "A truncated isoform of TMEFF2 encodes a secreted protein in prostate cancer cells," Genomics, 87(5):633-7 (2006).
Herman et al., "Methylation-specific PCR: A novel PCR assay for methylation status of CpG islands," Proc. Natl. Acad. Sci. USA, 93:9821-6 (1996).
Xiong et al., "COBRA: a sensitive and quantitative DNA methylation assay," Nucleic Acids Research, 25(12): 2532-4 (1997).
Cottrell et al., "A real-time PCR assay for DNA-methylation using methylation-specific blockers," Nucleic Acids Research, 32(1):e10 (2004).
Eads et al., "MethyLight: a high-throughput assay to measure DNA methylation," Nucleic Acids Research, 28(8): e32 (2000).
Gonzalgo et al., "Rapid quantitation of methylation differences at specific sites using methylation-sensitive single nucleotide primer extension (Ms-SNuPE)," Nucleic Acids Research, 25 (12):2529-31 (1997).
Fraga et al., "DNA Methylation: A Profile of Methods and Applications," BioTechniques, 33:632-49 (2002).
Brena et al., Quantitative assessment of DNA methylation: potential applications for diagnosis, classification, and prognosis in clinical settings, J. Mol Med., 84:365-77 (2006).

* cited by examiner

*Primary Examiner* — Jehanne Sitton
(74) *Attorney, Agent, or Firm* — Kriegsman & Kriegsman

(57) ABSTRACT

The present invention relates to a method for methylation analysis. It comprises the providing of a double stranded nucleic acid; its conversion, whereby unmethylated bases become distinguishable in their base-pairing behavior from methylated bases, and the analysis of both of the converted nucleic acid strands.

7 Claims, 10 Drawing Sheets

HQM Assay Design for TMEFF 2 a) HM reaction specific for unmethylation

TMEFF 2 genomic region after bisulfite conversion (upper strand; SEQ ID NO: 10):

5'-GAAAGAGAAAAGGtTttTtGtATAtGttGtCGCGTGGGTTGttGGGAGtATgGttGGtAGtGGtGTttGGGAAGGGAGAGtGGGtTttATTtGTtGGtttAGGtAGTGAtt-3' forward primer B (SEQ ID NO: 5)    5'-gaaagagaaaggtttttgtatac-3'
reverse primer B (SEQ ID NO: 6)    5'-aatcactacctaaaccaacaaata-3'
blocker B (SEQ ID NO: 7)           5'-gtataCGtCGCGgggtgggttgtCG-PH-3'
probe B (SEQ ID NO: 8)             5'-HEX-cttcccaaacaccactacccaa-BHQ-3' b) HM reaction specific for methylation

TMEFF 2 genomic region after bisulfite conversion (lower strand; SEQ ID NO: 11):

5'-aAAAaAAAAaaCTCCTCTaCATACGCCGCGGaaTaaaTTaCCGaaAaCATCGaCCGaaCAaCGaCGTCCGaaAAaaaAaAaCGaaCTCCATTTaTTaaCCCAaaCAaTaACC-3' forward primer A (SEQ ID NO: 1)    5'-aaaaaaaaaaactcctctacatac-3'
reverse primer A (SEQ ID NO: 2)    5'-ggttattgtttgggttaataaatg-3'
blocker A (SEQ ID NO: 3)           5'-aCATACaCCaCaaTaaaTTaCCaaaAaCATCaaCCaa-PH-3'
probe A (SEQ ID NO: 4)             5'-FAM-ttCGgaCGtCGttgttCGg-BHQ-3'

QM Assay Design for TMEFF 2

TMEFF 2 genomic region after bisulfite conversion (lower strand; SEQ ID NO: 11):

5'-aAAAaAAAAaaCTCCTCTaCATACGCCGCGGaaTaaaTTaCCGaaAaCATCGaCCGaaCAaCGaCGTCCGaaAAaaaAaAaCGaaCTCCATTTaTTaaCCCAaaCAaTaACC-3' forward primer A (SEQ ID NO: 1)    5'-aaaaaaaaaaactcctctacatac-3'
reverse primer A (SEQ ID NO: 2)    5'-ggttattgtttgggttaataaatg-3'
probe A (SEQ ID NO: 4)             5'-FAM-ttCGgaCGtCGttgttCGg-BHQ-3'
*probe C (SEQ ID NO: 9)*           *5'-HEX-TCaaCCaaaCAaCaaCaTCCaa-BHQ-3'*

Fig. 2

METHOD FOR METHYLATION ANALYSIS OF NUCLEIC ACID

FIELD OF THE INVENTION

The invention relates generally to novel and substantially improved methods for sensitive methylation analysis of nucleic acid. In particular it relates to sensitive and/or specific quantitative detection of methylated or unmethylated positions.

BACKGROUND OF ASPECTS OF THE INVENTION

It is well known in the art that DNA as well as RNA can be methylated. The base 5-methylcytosine is the most frequent covalently modified base found in the DNA of eukaryotic cells. DNA methylation plays an important biological role in, for example, regulating transcription, genetic imprinting, and tumorigenesis (for review see, e.g., Millar et al.: Five not four: History and significance of the fifth base; in *The Epigenome*, S. Beck and A. Olek (eds.), Wiley-VCH Publishers, Weinheim 2003, pp. 3-20). The identification of 5-methylcytosine is of particular interest in the area of cancer diagnosis. But the identification of methylation is difficult. Cytosine and 5-methylcytosine have the same base-pairing behavior, making 5-methylcytosine difficult to detect using particular standard methods. The conventional DNA analysis methods based on hybridization, for example, are not applicable. In addition, the methylation information is lost completely by the amplification by means of PCR.

Accordingly, current methods for DNA methylation analysis are based on two different approaches. The first approach utilizes methylation specific restriction enzymes to distinguish methylated DNA, based on methylation specific DNA cleavage. The second approach comprises selective chemical conversion (e.g., bisulfite treatment; see e.g. WO 2005/038051) of unmethylated cytosines to uracil while methylated cytosines remain unchanged. Uracil has the same base pairing behavior as thymine. It therefore forms base pairs with adenine. Instead, 5-methylcytosine hybridizes with guanine still after bisulfite treatment. It is therewith possible to differentiate between methylated and unmethylated cytosines. The enzymatically or chemically pretreated DNA generated in these approaches is typically pre-amplified and analyzed in different ways (see, e.g., WO 02/072880 pp. 1 ff; Fraga and Estella: DNA methylation: a profile of methods and applications; Biotechniques, 33:632, 634, 636-49, 2002). The pre-amplification of chemically pretreated DNA leads to an enhanced sensitivity of the subsequent detection reaction.

Different PCR methods are known in the art for analyzing converted and unconverted cytosine positions. Selective amplification only of unconverted (methylated) or with the reverse approach, converted (unmethylated) cytosine positions is attained by using methylation specific primers in so-called methylation-specific PCR (MSP) methods, or by using 'blockers' in "HeavyMethyl™" methods (see, e.g., Herman et al.: Methylation specific PCR: a novel PCR assay for methylation status of CpG islands. *Proc Natl Acad Sci USA*. 93:9821-6, 1996; Cottrell et al.: A real-time PCR assay for DNA-methylation using methylation specific blockers. *Nucl. Acids Res.*, 32:e10, 2004). Alternatively, it is possible to amplify the DNA in a non-methylation specific manner, and analyze the amplificates by means of methylation specific probes (see, e.g., Trinh et al.: DNA methylation analysis by MethyLight technology. *Methods*, 25:456-62, 2001). Particular PCR-based methods are also applicable as 'real-time' PCR variants, making it possible to detect the methylation status directly in the course of the PCR, without the need for a subsequent analysis of the products (MethyLight™; WO 00/70090; U.S. Pat. No. 6,331,393; and Trinh et al. 2001, supra).

Quantification of the degree of DNA methylation is required in many applications including, but not limited to, classification of tumors, obtaining prognostic information, or for predicting drug effects/responses. Different methods of such quantification are known in the art, such as 'end-point analysis' and 'threshold-value analysis'.

End-point, analyses: To some extend, the DNA is pre-amplified, like for example in the Ms-SNuPE method, for the hybridization on microarrays, for hybridization assays in solution or for direct bisulfite sequencing (see, e.g., Fraga and Estella 2002, supra). A problem with such "end point analyses" (where the amplificate quantity is determined at the end of the amplification) is that the amplification can occur non-uniformly because of, inter alia, obstruction of product, enzyme instability and/or a decrease in concentration of the reaction components. Correlation between the quantity of amplificate, and the quantity of DNA utilized is, therefore, not always suitable, and quantification is thus sensitive to error (see, e.g., Kains: The PCR plateau phase—towards an understanding of its limitations. *Biochem. Biophys. Acta* 1494:23-27, 2000).

Threshold-value analyses: By contrast, threshold-value analysis, which is based on a real-time PCR, determines the quantity of amplificate in the exponential phase of the amplification, rather than at the end of the amplification. Such threshold, real-time methods presume that the amplification efficiency is constant in the exponential phase. The art-recognized threshold value 'Ct' is a measure corresponding, within a PCR reaction, to the first PCR cycle in which the signal in the exponential phase of the amplification is greater than the background signal. Absolute quantification is then determined by means of a comparison of the Ct value of the investigated (test) DNA with the Ct value of a standard (see, e.g., Trinh et al. 2001, supra; Lehmann et al.: Quantitative assessment of promoter hypermethylation during breast cancer development. *Am J Pathol.*, 160:605-12, 2002). A substantial problem of such Ct value-based analyses is that when high DNA concentrations are used, only a small resolution can be achieved. This problem also applies when high degrees of methylation are determined via PMR values (for discussion of PMR values see, e.g., Eads et al., *CANCER RESEARCH* 61:3410-3418, 2001.) Additionally, amplification of a reference gene (e.g., the β-actin gene) is also required for this type of Ct analysis (see, e.g., Trinh et al. 2001, supra). (An overview of real time PCR based quantification can be obtained from WO 2005/098035; Real-Time PCR: An Essential Guide, Horizon Bioscience, Kirstin Edwards, Julie Logan and Nick Saunders, May 2004 ISBN: 0-9545232-7X; Real-time PCR, M. Tevfik Dorak, Taylor & Francis, April 2006), ISBN: 041537734X; Mackay I M, Arden K E, Nitsche A. Real-time PCR in virology. Nucleic Acids Res. 2002 Mar. 15; 30(6):1292-305; Bernard P S, Wittwer C T. Real-time PCR technology for cancer diagnostics. Clin Chem. 2002 August; 48(8):1178-85; Bernhard Kaltenboeck and Chengming Wang. Advances in real-time PCR: Application to clinical laboratory diagnostics. Advances in Clinical Cancer, 2005; 40:219-259).

A critical parameter for methylation analysis is sensitivity. The reason for this is the problem that samples to be analyzed usually comprise heterogeneous DNA. The DNA is of the same sequence but has a different methylation. Thereby, DNA with a sought methylation pattern is only present in low amounts. An example is the tumor diagnosis out of body fluids. The death of tumor cells results in a release of tumor DNA into body fluids like blood. But also the DNA of died healthy cells is found in the blood. Various levels of tumor DNA are found besides non-tumor DNA depending on the size and the progression of the cancer disease. Because of obvious reasons, an early as possible detection of a tumor is favorable. This means that the slightest amount of tumor DNA has to be reliable detected and correctly analyzed during methylation analysis. As more sensitive a method for methylation analysis is as more early tumor DNA can be detected and a tumor can be diagnosed.

Another example is the detection of a cell type by detection of its specific methylation in a biopsy sample comprising various cell types. Thereby, the presence or absence of said cell type may be indicative for a disease or for a likely respond to a treatment. Also in this case the slightest amount of cell type specific DNA has to be reliable detected and correctly analyzed by methylation analysis Therefore it is a major concern in the field of the art exists to improve the sensitivity of known methods for methylation analysis or to provide new methods with a high as possible sensitivity.

The method for methylation analysis with the so far highest specificity is the real time QM method (quantitative methylation method; WO 2005/098035). Here a non-methylation specific, conversion specific amplification of the target DNA is performed. The amplificates are detected by means of the hybridization of two different methylation specific real-time PCR probes. Thereby one of the probes is specific for the methylated state, while the other probe is specific for the unmethylated state. The two probes bear different fluorescent dyes. A quantification of the degree of methylation is obtained within specific PCR cycles employing the ratio of signal intensities of the two probes. Alternatively, the Ct values of two fluorescent channels can also be drawn on for the quantification of the methylation.

Because of obvious reasons, another major concern in the art exists in providing methylation analysis methods which ensure a high as possible sensitivity. This means for example that as much as possible of all samples derived from individuals having cancer are detected within a group of samples derived from individuals having cancer or not.

The method for methylation analysis with the so far highest specificity is an embodiment of the above mentioned HeavyMethyl™ method in which methylation specific blockers and probes are used in real time PCR. Thereby the blocker is specific for certain unmethylated cytosine position(s) while the probe is specific for the same cytosine position(s) being methylated, or vice versa.

Currently the applicant is not aware of any method with a greater specificity as the QM method or a greater sensitivity as the HM method.

DETAILED DESCRIPTION OF ASPECTS OF THE INVENTION

For achieving various technical objects, particular aspects of the invention teach and provide a method for methylation analysis of nucleic acid, comprising
providing double stranded nucleic acid,
converting said nucleic acid in such a way that 5-methyl-cytosine remains unchanged, while unmethylated cytosine is converted to uracil or to another base that is distinguished by cytosine in its base-pairing behavior, said reaction leading to two different converted DNA strands that are no longer complementary to each other, and
analyzing both of the converted nucleic acid strands, wherein at least one of the both strands in analyzed in a methylation specific reaction.

Particular aspects of the invention teach and provide a method for methylation analysis of nucleic acid characterized by high sensitivity. Thereby one of the converted nucleic acid strands is analyzed with respect to the presence of methylation of one or more cytosine positions while the other converted strand is analyzed with respect to the absence of methylation of the same one or more positions. Particular aspects of the invention teach and provide a method for methylation analysis of nucleic acid characterized by a high specificity. Thereby, either both of the converted nucleic acid strands are analyzed with respect to the presence of methylation of one or more cytosine positions or with respect to the absence of methylation. Particular aspects of the invention teach and provide a method for methylation analysis of nucleic acid characterized in that the copy number of the analyzed positions is considered simultaneously. Thereby one of the two converted nucleic acid strands is analyzed with respect to the presence or absence of methylation. The other converted strand is analyzed non-methylation specifically at a correspondent region. Particular aspects of the invention teach and provide a method for methylation analysis of nucleic acid characterized that the normalization to a reference region occurs simultaneously. Thereby one of the two converted nucleic acid strands is analyzed with respect to the presence or absence of methylation. The other converted strand is analyzed non-methylation specifically at a non-correspondent reference region.

Particular aspects of the invention teach a kit for methylation analysis of nucleic acid. Particular aspects of the invention teach the use of the herein taught and provided methods as well as the herein taught kit.

ADVANTAGES OF ASPECTS OF THE INVENTION

Particular aspects of the invention are characterized in that they have an enhanced sensitivity when compared to conventional methods for methylation analysis. The enhanced sensitivity is based in that the presence of methylation and the absence of methylation are detected simultaneously by use of the same double stranded nucleic acid molecule. In contrast, conventional methods for DNA methylation analysis like for example Ms-SNuPE, MSP, HeavyMethyl™, MethyLight™, or QM also start with a double stranded molecule, but consider after bisulfite conversion only one of the two converted strands. Thereby either only the presence of methylation or the absence of methylation is detected (Gonzalgo et al. "Rapid quantitation of methylation differences at specific sites using methylation-sensitive single nucleotide primer extension (Ms-SNuPE)". Nucleic Acids Research, 1997, 25 (12), 2529-2531; Herman et al.: supra; Cottrell et al.: supra; Trinh et al.: supra; WO 2005/098035). This is in clear contrast to aspects of the invention, wherein simultaneously the presence of methylation and the absence of methylation is analyzed.

The method of the invention shows an enhanced sensitivity, when compared with the QM method, the method with the so far best known sensitivity (see Example 1). The method of the invention, in contrast to the QM method, is able to reliable resolve methylation results below 10% methylation or unmethylation and above 90% unmethylation or methylation. It is even able to reliable detect methylation or unmethylation in the range of 0-1% and 99-100%, respectively (see FIGS. 3-6).

Particular aspects of the invention are characterized in that they have an enhanced specificity when compared to conventional methods for methylation analysis. The enhanced specificity is based in that the presence of methylation is detected simultaneously for both of the converted strands of the provided double stranded nucleic acid molecule. Of course also the absence of methylation is detectable accordingly. In contrast, conventional methods for DNA methylation analysis such as Ms-SNuPE, MSP, HeavyMethyl™, MethyLight™, or QM also start with a double stranded molecule, but consider after bisulfite conversion only one of the two converted strands (Gonzalgo et al.: supra; Herman et al.: supra; Cottrell et al.: supra; Trinh et al.: supra; WO 2005/098035). Only WO 99/28498 suggested to consider both strands (WO 99/28498 bridging paragraph p 22-23). However not as the method of the invention in one detection reaction leading to one result but rather in two separate reactions, wherein one result is a independent control of the other. This has the effect that the variance of the results is minimized. But it has no influence on the specificity.

Particular aspects of the invention are characterized in that methylation results are simultaneously normalized to the copy number of the analyzed positions. This simultaneous normalization is achieved by analyzing the methylation of positions on one strand of the double stranded nucleic acid molecule and the copy number of the said positions on the other strand. Conventional methods like Ms-SNuPE, MSP, HeavyMethyl™, MethyLight™, or QM in contrast do not consider simultaneously the copy number of the analyzed positions (Gonzalgo et al.: supra; Herman et al.: supra; Cottrell et al.: supra; Trinh et al.: supra; WO 2005/098035). In fact, the detection of the copy number occurs in a different separate experiment. The normalization occurs subsequent of the detection reactions.

Particular aspects of the invention are characterized in that methylation results are simultaneously normalized to a reference region. This simultaneous normalization is achieved by analyzing the methylation of positions on one strand of the double stranded nucleic acid molecule and a reference region on the other strand. Conventional methods like Ms-SNuPE, MSP, HeavyMethyl™, MethyLight™, or QM in contrast do not consider simultaneously a reference region (Gonzalgo et al.: supra; Herman et al.: supra; Cottrell et al.: supra; Trinh et al.: supra; WO 2005/098035). In fact, the detection of a reference region occurs in a different separate experiment. The normalization occurs subsequent of the detection reactions.

Particular aspects of the invention have the advantage that a reduced amount of nucleic acid is necessary when compared to conventional methods like Ms-SNuPE, MSP, HeavyMethyl™, MethyLight™, or QM. According to the invention both strand of the provided double stranded nucleic acid are further analyzed. In contrast thereto, according to conventional methods only one strand after bisulfite conversion is analyzed in one reaction. Extra amounts of DNA are necessary either for normalization to the copy number of the analyzed position or positions or to a reference region, or for confirmation of the methylation results. Many times the amount of nucleic acid which is available for analysis is very limited. This is especially the case when the nucleic acid is isolated from body fluids or biopsis in particular formalin-fixed material.

Particular aspects of the invention have the advantage that they are less time consuming in comparison to conventional methods. According to the invention both strands of the provided double stranded nucleic acid are analyzed simultaneously in one reaction. In the contrary, according to conventional methods, methylation is analyzed in one experiment (Ms-SNuPE, MSP, HeavyMethyl™, MethyLight™, or QM). A confirmation or normalization of the results can only be achieved by further experiments which have to be performed separately. This is time consuming with respect to the working time as well as to the run time of machines.

Particular aspects of the invention have the advantage that they minimize the handling effort in comparison to conventional methods. According to the invention both strands of the provided double stranded nucleic acid are analyzed simultaneously in one reaction. In the contrary, according to conventional methods, methylation is analyzed in one experiment (Ms-SNuPE, MSP, HeavyMethyl™, MethyLight™, or QM). A confirmation or normalization of the results can only be achieved by further experiments which have to be performed separately. This results in a larger handling effort as it is necessary for the method of the invention.

Because of the said advantages, the method of the invention is in particular suitable for high-throughput procedures. It is also suitable for manual as well as for automatic implementation.

METHOD OF ASPECTS OF THE INVENTION

Aspects of the present invention relate to a method for methylation analysis. The method of the invention comprises the providing of a double stranded nucleic acid; its conversion, whereby unmethylated bases become distinguishable in their base-pairing behavior from methylated bases; and the analysis of both of the converted nucleic acid strands. The method is a method for the detection of the presence of one or more methylated or unmethylated cytosine bases. The cytosines to be analyzed thereby can be co-methylated or not. Single or multiple cytosines co-methylated or not are known to a person skilled in the art as methylation pattern. The method of the invention enables the analysis not only with respect to one double stranded nucleic acid molecule but also with respect to a plurality of molecules. Thereby one or more methylation pattern are detectable as well as quantifiable. Thus, it is determinable the degree of methylation and/or the percentage of molecules with a certain methylation pattern. This is for example indicated for the analysis of DNA derived from tissue or body fluids samples, which comprise not only tumor cells but also benign cells. The method of the invention is then able to detect and quantify a methylation pattern specific for the tumor within the mixture of tumor and benign DNA.

The method of the invention is a method for methylation analysis of nucleic acid, comprising
providing double stranded nucleic acid,
converting said nucleic acid in such a way that 5-methylcytosine remains unchanged, while unmethylated cytosine is converted to uracil or to another base that is distinguished by cytosine in its base-pairing behavior, said reaction leading to two different converted nucleic acid strands that are no longer complementary to each other,
analyzing both of the converted nucleic acid strands.

In a preferred embodiment, the providing of double stranded nucleic acid comprises at least one of the following: obtaining a tissue or body fluid sample from an individual; isolating a double stranded nucleic acid molecule from said sample; purifying a double stranded nucleic acid; and fragmenting a double stranded nucleic acid by biological, chemical or physical means like for example but not limited to enzymatic digestion or sonication. In a preferred embodiment, the enzymatic digestion comprises the digestion with either non-methylation specific enzymes, methylation specific enzymes, or both.

A preferred embodiment comprises that analyzing both of the converted nucleic acid strands comprises a simultaneous analysis.

A preferred embodiment comprises that the methylation of one of the original provided nucleic acid strands is analyzed.

In a preferred embodiment, the analysis of both of the converted nucleic acids strands comprises that at least one of the both strands in analyzed in a methylation specific reaction.

A preferred embodiment comprises that the methylation of both of the original provided nucleic acid strands is analyzed.

In a preferred embodiment both of the two converted nucleic acid strands are analyzed in a methylation specific reaction. Thereby said methylation specific reaction is for example but not limited to it a methylation specific amplification. This embodiment is illustrated by FIG. 1.

In a preferred embodiment either a) the presence or absence of one or more methylation pattern is analyzed of both converted strands; or b) the presence or absence of one or more methylation pattern is analyzed of one converted strand and the presence or absence of other one or more methylation pattern is analyzed of the other converted strand.

In a preferred embodiment either a) the presence of methylation at one or more CpG positions of one converted strand and the absence of methylation at the same one or more CpG positions of the other converted strand is analyzed; or b) the presence or absence of methylation at the same one or more CpG positions of both converted strands is analyzed.

A preferred embodiment comprises the methylation analysis of at least one CpG position on both of the converted nucleic acid strands. Thereby methylation analysis means the presence or absence of cytosine methylation. In other words, two sets of CpG dinucleotides are analyzed, each set comprising at least one CpG dinucleotide. Thereby each set is located on one of the two complementary strands of the provided double stranded nucleic acid. Two CpG dinucleotides each of one set are part of one CpG position and they are lie opposite to each other.

A particular preferred embodiment comprises the detection of converted methylated cytosine at a CpG position on one converted strand and the detection of converted unmethylated cytosine at the same CpG position on the other strand. In other words, only one CpG positions is analyzed. The respective two CpG dinucleotides of said CpG position lie opposite to each other, each dinucleotide on one of the two complementary strands of the provided double stranded nucleic acid. The methylation of one cytosine and the non-methylation of the other correspondent cytosine is determined, in particular the degree of methylation and non-methylation is quantified. Accordingly, also two or more CpG positions are analyzable. This embodiment has the advantage that it is very sensitive. It is about 100 times more sensitive than comparable conventional methods known to those skilled in the art.

A particular preferred embodiment comprises the detection of converted methylated cytosine at the same CpG position on both converted strands. In other words, the two analyzed CpG dinucleotides lie opposite to each other, each on one of the two complementary strands of the provided double stranded nucleic acid. The methylation of the one another correspondent cytosines is determined, in particular the degree of their methylation is quantified. Accordingly, also two or more CpG positions are analyzable. This embodiment has the advantage that it is highly specific.

A particular preferred embodiment comprises the detection of converted unmethylated cytosine at the same CpG position on both converted strands. In other words, the two analyzed CpG dinucleotides lie opposite to each other, each on one of the two complementary strands of the provided double stranded nucleic acid. The non-methylation of the one another correspondent cytosines is determined, in particular the degree of their non-methylation is quantified. Accordingly, also two or more CpG positions are analyzable. This embodiment has the advantage that it is highly specific.

A preferred embodiment comprises the methylation analysis of at least one CpG position on one of the converted nucleic acid strands and the methylation analysis of different at least one CpG position on the other converted strand. Thereby methylation analysis means the presence or absence of cytosine methylation. In other words, two sets of CpG positions are analyzed, each comprising of two CpG dinucleotides being opposite located each on one of the strands. Only one of the said CpG dinucleotides per CpG position is analyzed, whereby two sets of CpG dinucleotides are formed. The CpG dinucleotides of the two sets do not lie opposite to each other. But each set is located on one of the two complementary strands of the provided double stranded nucleic acid. This embodiment has the advantage that different methylation patterns are analyzable simultaneously and independent from one another.

In a preferred embodiment either a) the presence or absence of methylation of one or more CpG positions is analyzed of both converted strands; or b) the presence or absence of methylation of one or more CpG positions is analyzed of one converted strand and the presence or absence of methylation of other one or more CpG positions is analyzed of the other converted strand.

In a preferred embodiment either a) the presence of one or more methylation pattern on one converted strand and the presence of the inversed one or more methylation pattern on the other converted strand is analyzed; or b) the presence or absence of one or more methylation pattern on both converted strands is analyzed.

In a preferred embodiment one of the two converted strands is analyzed in a methylation specific reaction and the other strand is analyzed in a methylation unspecific reaction. Preferably the presence or absence of one or more methylation pattern is analyzed. Preferably the presence or absence of methylation of one or more cytosines is analyzed.

A preferred embodiment comprises a methylation analysis of one converted strand and a non-methylation analysis of the other converted strand. Thereby a non-methylation analysis is for example but not limited to it an analysis of the copy number or an analysis of SNP. A methylation analysis is the analysis of the presence or absence of one or more methylation pattern or the presence of absence of methylation of one or more cytosines.

A preferred embodiment comprises a methylation analysis of one converted strand and a non-methylation analysis of the other converted strand. Thereby the methylation analysis and the non-methylation analysis cover corresponding, overlapping or adjacent sections on the strands of the provided double stranded nucleic acid. In either case two sections are considered, one on each strand. Two sections are corresponding, wherein both sections are reverse complementary to one another before conversion. But they are no longer reverse complementary after conversion. Two sections are overlapping sections, wherein both sections are partially reverse complementary to one another before conversion. But they are no longer reverse complementary after conversion. Two sections are adjacent sections, wherein one section is reverse complementary to a section on the respective other strand, whereby said reverse complementary section is immediately located before or after the other considered section. Adjacent sections are neither before nor after conversion reverse complementary to one another. This embodiment has the advantage that results of the methylation analysis of one section are simultaneously normalized to the copy number of the other corresponding, overlapping or adjacent section.

A preferred embodiment comprises a methylation analysis of one converted strand and a non-methylation analysis of the other converted strand. Thereby the methylation analysis and the non-methylation analysis cover different sections on the strands of the provided double stranded nucleic acid. Two sections are different, wherein both sections are not reverse complementary to one another before conversion and wherein the reverse complementary section of one section is not immediately located before or after the other considered section. Different sections are neither before nor after conversion reverse complementary to one another. This embodiment has the advantage that results of the methylation analysis of one section are simultaneously normalized to a different section as a reference region.

In a preferred embodiment, the nucleic acid is DNA, genomic DNA or RNA.

A preferred embodiment, comprises the methylation analysis of DNA. This DNA can be genomic DNA or methylated non-genomic DNA. Preferably the analyzed DNA is genomic DNA. A preferred embodiment comprises the methylation analysis of RNA. A preferred embodiment comprises the methylation analysis of artificially methylated PNA. A preferred embodiment comprises the methylation analysis of methylated DNA, RNA or PNA analogs.

In a preferred embodiment, the analysis of both converted strands comprises the analysis of SNP.

A preferred embodiment, comprises the analysis of mutations, of deletion or amplification of one or more adjacent nucleotides, or of copy number. Preferably such an analysis occurs in a methylation unspecific reagent.

In a preferred embodiment, the converting of nucleic acid comprises a chemical reagent, bisulfite, an enzyme, or a cytidin-deaminase.

In a preferred embodiment, the converting of nucleic acid comprises a chemical reagent or enzyme, preferably it comprises bisulfite or a cytidin-deaminase.

A preferred embodiment comprises a bisulfite conversion. A bisulfite conversion comprises a treatment with a bisulfite, a disulfite or a hydrogensulfite solution. As known to those skilled in the art and according to the invention, the term "bisulfite" is used interchangeably for "hydrogensulfite" or "disulfite". Several laboratory protocols are known in the art (e.g.: Frommer et al. (1992) A genomic sequencing protocol that yields a positive display of 5-methylcytosine residues in individual DNA strands. Proc Natl Acad Sci U.S.A.; 89(5): 1827-1831). Preferably a bisulfite conversion is performed as essentially described in Olek A. et al. (Olek et al. "A modified and improved method for bisulphite based cytosine methylation analysis", *Nucl. Acids Res.* 24, 5064-5066, 1996), WO 01/98528, WO 03/038121, WO 04/067545, WO 05/038051, WO 06/040187, WO 06/039563, PCT/EP2006/003193, or PCT/US2006/014667.

It is preferred that the bisulfite treatment is performed in an agarose block. It is preferred that the bisulfite treatment is performed in the presence of a denaturing solvent, such as, but not limited to, n-alkylenglycol, particularly diethylene glycol dimethyl ether (DME), or in the presence of dioxane or dioxane derivatives. Preferably, the denaturing solvents are used in concentrations between 1% and 35% (v/v). It is also preferred that the bisulfite reaction is carried out in the presence of scavengers such as, but not limited to, chromane derivatives, e.g. 6-hydroxy-2,5,7,8-tetramethylchromane 2-carboxylic acid or trihydroxybenzoe acid and derivates thereof, e.g. Gallic acid. The bisulfite conversion is preferably carried out at a reaction temperature between 30° C. and 70° C., whereby the temperature is increased to over 85° C. for short periods of times during the reaction. The bisulfite-treated DNA is preferably purified prior to the quantification. This may be conducted by any means known in the art, such as, but not limited to, ultrafiltration, preferably carried out by means of Microcon™ columns (manufactured by Millipore™). The purification is carried out according to a modified manufacturer's protocol, for example, but not limited to it, see WO 05/038051. Preferably body fluid samples or archived samples are pretreated, bisulfite treated and purified as described in PCT/US2006/014667 or WO 06/039563.

Preferably, the bisulfite conversion is conducted as described in Olek et al. "A modified and improved method for bisulphite based cytosine methylation analysis", *Nucl. Acids Res.* 24, 5064-5066, 1996), WO 01/98528, WO 03/038121, WO 04/067545, WO 05/038051, WO 06/040187, WO 2006/039563, PCT/EP2006/003193, or PCT/US2006/014667.

In a preferred embodiment, the converting of nucleic acid comprises one or more nucleic acid converting enzymes. Preferably, but not limited to, such enzymes are cytidine-deaminases. Cytidine-deaminase converts unmethylated cytidine faster as unmethylated cytidine. An appropriate enzyme is described by Bransteitter et al. (Bransteitter et al.: "Activation-induced cytidine deaminase deaminates deoxycytidine on single-stranded DNA but requires the action of Rnase". PNAS 2003, 100(7): 4102-4107; WO 2005/005660).

In a preferred embodiment, analyzing both of the converted nucleic acid strands comprises the analysis of corresponding, overlapping, adjacent or different sections of the strands of the originally provided nucleic acid.

In a preferred embodiment, analyzing both of the converted nucleic acid strands comprises the analysis of at least one of the following: same genes or genomic regions, associated genes or genomic regions, independent genes or genomic regions, comethylated genes or genomics region, or not comethylated genes or genomic regions.

In a preferred embodiment, analyzing both of the converted nucleic acid strands comprises the analysis of one or more CpG positions located on a converted strand and the analysis of a corresponding section located on the other converted strand.

A preferred embodiment, comprises the analysis of one or more methylation pattern on one converted strand and the analysis of the correspondingly located one or more sections on the other converted strand.

In a preferred embodiment, analyzing both of the converted nucleic acid strands comprises the analysis of one or more CpG positions located on a converted strand and the analysis of a non-corresponding section located on the other converted strand.

A preferred embodiment, comprises the analysis of one or more methylation pattern on one converted strand and the analysis of non-correspondingly located one or more sections on the other converted strand.

In a preferred embodiment, analyzing both of the converted nucleic acid strands comprises the quantification of methylation or non-methylation of one or more CpG positions, the quantification of converted nucleic acid, the quantification of unconverted nucleic acid, or combinations thereof. The quantification of converted or unconverted nucleic acid occurs by the quantification of one strand after conversion. The quantification of converted nucleic acid on correspondent, overlapping, adjacent or different sections of the two converted strands is indicated for normalization of one or more methylation pattern. The quantification of unconverted nucleic acid is indicated for controlling the nucleic acid conversion. The quantification of methylation or non-methylation of one or more CpG positions is indicated for identification and/or detection of one or more methylation pattern.

In a preferred embodiment, the quantification of methylation or non-methylation of one or more CpG positions, the quantification of converted nucleic acid, or the quantification of unconverted nucleic acid comprises standards, real time PCR quantification algorithms, or both. Suitable methods are known to those skilled in the art. Preferably a quantification occurs as described in PCT/EP2005/003793; Real-Time PCR: An Essential Guide, Horizon Bioscience, Kirstin Edwards, Julie Logan and Nick Saunders, May 2004 ISBN: 0-9545232-7X; Real-time PCR, M. Tevfik Dorak, Taylor & Francis, April 2006, ISBN: 041537734X; Mackay IM, Arden KE, Nitsche A. Real-time PCR in virology. Nucleic Acids Res. 2002 Mar. 15; 30(6):1292-305; Bernard P S, Wittwer C T. Real-time PCR technology for cancer diagnostics. Clin Chem. 2002 August; 48(8):1178-85; or Bernhard Kaltenboeck and Chengming Wang. Advances in real-time PCR: Application to clinical laboratory diagnostics. Advances in Clinical Cancer, 2005; 40:219-259. Quantification is also possible relative to one another, for example, but not limited to, the amount of converted nucleic acid is "x"-time of the amount of unconverted nucleic acid or the degree of methylation of CpG position "y" is "x"-time higher than the degree of methylation of CpG position "z".

In a preferred embodiment analyzing both of the converted nucleic acid strands comprises at least one selected from the group comprising: amplification method, PCR method, isothermal amplification method, NASBA method, LCR method, methylation specific amplification method, MSP (methylation specific PCR) method, nested MSP method, HeavyMethyl™ method, detection method, methylation specific detection method, bisulfite sequencing method, detection by means of microarrays, detection by means of oligonucleotide microarrays, detection by means of restriction enzymes, simultaneous methylation specific amplification and detection method, real-time PCR, HeavyMethyl™ real time PCR method, MSP MethyLight™ method, MethyLight™ method, MethyLight™ Algo™ method, QM method, Headloop MethyLight™ method, HeavyMethyl™ MethyLight™ method, HeavyMethyl™ Scorpion™ method, MSP Scorpion™ method, Headloop Scorpion™ method, methylation sensitive primer extension, and Ms-SNuPE (Methylation-sensitive Single Nucleotide Primer Extension) method.

Preferably, the analysis of the two nucleic acid strands after conversion comprises at least one method selected from the group comprising: amplification method, PCR method, isothermal amplification method, NASBA method, LCR method, methylation specific amplification method, MSP (methylation specific PCR) method, nested MSP method, HeavyMethyl™ method, detection method, methylation specific detection method, bisulfite sequencing method, detection by means of microarrays, detection by means of oligonucleotide microarrays, detection by means of restriction enzymes, simultaneous methylation specific amplification and detection method, real-time PCR, HeavyMethyl™ real time PCR method, MSP MethyLight™ method, MethyLight™ method, MethyLight™ Algo™ method, QM method, Headloop MethyLight™ method, HeavyMethyl™ MethyLight™ method, HeavyMethyl™ Scorpion™ method, MSP Scorpion™ method, Headloop Scorpion™ method, methylation sensitive primer extension, and Ms-SNuPE (Methylation-sensitive Single Nucleotide Primer Extension) method.

According to an embodiment, the amplification method can be any kind of amplification method. A person skilled in the art is in knowledge of suitable amplification methods. According to a preferred embodiment, the amplification method is a PCR method. A person skilled in the art knows suitable PCR methods which can be used according to the invention. According to a preferred embodiment, the amplification method is an isothermal amplification. Suitable amplification methods for use according to the invention are well known in the art. Such a method can be, for example, but not limited to it, the primer extension method. According to a preferred embodiment, the amplification method is a NASBA method. NASBA methods are RNA-DNA based amplification methods which comprise the use of a Reverse Transcriptase, a RNA polymerase and a RNase. A person skilled in the art is aware of NASBA methods which can be used according to the invention. According to a preferred embodiment, the amplification method is a Ligase Chain Reaction method. In general, these are amplification methods which are based on the use of a ligase. A person skilled in the art knows suitable LCR which can be used according to the invention.

According to an embodiment, the amplification method is a methylation specific amplification. Suitable methylation specific amplification methods are known to those skilled in the art. According to a preferred embodiment, the methylation specific amplification method is the methylation specific PCR (MSP) method. The MSP method allows the assessing of methylation of CpG dinucleotides (see above; Herman et al.: supra; U.S. Pat. No. 5,786,146).

Briefly, bisulfite converted DNA is amplified with primers specific for methylated versus unmethylated DNA. MSP primer pairs contain at least one primer, which hybridizes to a bisulfite converted CpG dinucleotide. Therefore, the sequence of said primers comprises at least one CpG dinucleotide. MSP primers specific for non-methylated DNA contain a "T" at the 3' position of the C position in the CpG. Preferably, therefore, the base sequence of said primers is required to comprise a sequence having a length of at least 9 nucleotides which hybridizes to the bisulfite converted nucleic acid sequence, wherein the base sequence of said oligomers comprises at least one CpG dinucleotide. MSP requires only small quantities of DNA and is sensitive to 0.1% methylated alleles of a given CpG island locus.

According to a preferred embodiment, the amplification is a nested MSP method. The nested MSP method is essentially carried out as described in WO 02/18649 and US 20040038245. This MSP method comprises the expanding of Copy numbers of the genetic region of interest after bisulfite conversion. Therefore a polymerase chain reaction is used to amplify a portion of said region wherein the methylation of interest resides. Thereby an amplification product is generated. An aliquot of said product is then used in a second, methylation specific, polymerase chain reaction to detect the presence of methylation. In other words a non methylation specific PCR is performed prior to the methylation specific PCR.

According to a preferred embodiment, the amplification method is the HeavyMethyl™ method. The HeavyMethyl™ method is essentially carried out as described in WO 02/072880 and Cottrell et al. (Cottrell et al. Nucleic Acids Res. 2004 Jan. 13; 32(1):e10). This method comprises the use of blocking probe oligonucleotides which may be hybridized to the bisulfite treated template nucleic acid concurrently with the PCR primers. Preferably, the blocking oligonucleotides are characterized in that their base sequence comprises a sequence having a length of at least 9 nucleotides which hybridizes to the chemically treated nucleic acid sequence. Thereby the base sequence of said blocker oligonucleotides comprises at least one CpG, TpG or CpA dinucleotide. The amplification of the template nucleic acid is suppressed in case the complementary sequence of the blocking probe is present in the template. In such a case the amplification is terminated at the 5' position of the blocking probe. The blocking probe may be designed to hybridize to the bisulfite treated nucleic acid in a methylation status specific manner. For example, methylated nucleic acids within a population of unmethylated nucleic acids can be detected by suppressing the amplification of nucleic acids which are unmethylated at a position in question. Therefore a blocking probe would comprise a 'CpA' or 'TpA' at the position in question, as opposed to a 'CpG' if the suppression of amplification of methylated nucleic acids is desired. The use of blocker oligonucleotides requires for a efficient disruption of polymerase-mediated amplification that the blocker oligonucleotides can not be elongated by the polymerase. According to the HeavyMethyl™ method, this is achieved through the use of blockers that are 3'-deoxyoligonucleotides, or oligonucleotides derivatized at the 3' position with other than a "free" hydroxyl group. For example, but not limited to it, 3'-O-acetyl oligonucleotides are representative of a preferred class of blocker molecules.

Additionally, polymerase-mediated degradation of the blocker oligonucleotides should be precluded. Preferably, such preclusion comprises either i) the use of a polymerase lacking 5'-3' exonuclease activity, or ii) the use of modified blocker oligonucleotides. These modified blocker oligonucleotides are characterized in having, for example, thioate bridges at the 5'-terminii. This renders the blocker molecule nuclease-resistant. Particular applications may not require such 5' modifications of the blocker oligonucleotide. For example, degradation of the blocker oligonucleotide will be substantially precluded if the blocker- and primer-binding sites overlap. Thereby the binding of the primer is precluded (e.g., in case of excess blocker oligonucleotide). Therefore the polymerase can not bind on the primer and elongated it. Because no polymerase is extending the primer, the blocking oligonucleotide will not be degraded. A particularly preferred embodiment of the HeavyMethyl™ method, for purposes of the present invention and as implemented herein, comprises the use of peptide nucleic acid (PNA) oligomers as blocking oligonucleotides. Such PNA blocker oligomers are ideally suited because they are neither degraded nor extended by the polymerase.

According to an embodiment, the detection method can be any kind of detection method. A person skilled in the art is in knowledge of suitable detection methods. Preferably, a detection method can be any kind of detection method which comprises the use of a fluorescent dye, a non-fluorescent dye, a mass label, a separation by size, or a separation by weight. For example, but not limited to it, the detection method is a separation by size in an agarose gel followed by a staining of DNA by means of a fluorescent dye. According to a preferred embodiment, the detection method is a methylation specific detection. A person skilled in the art knows suitable methylation specific detection methods. According to a preferred embodiment, the methylation specific detection method is a bisulfite sequencing method. The bisulfite sequencing method is essentially carried out as described in Frommer et al. (Frommer et al. Proc. Natl. Acad. Sci. USA 89:1827-1831, 1992). The bisulfite sequencing method is a method wherein the sequencing of a previously amplified fragment of the bisulfate treated genomic DNA is carried out. As the bisulfite treated DNA is amplified before sequencing, an amplification method as described herein may be used in combination with this detection method. It is further especially preferred that the results of a bisulfite sequencing are essentially analyzed as described in EP 02090203. In brief, according to this method the degree of methylation of a cytosine is determined by means of an electropherogram of one or more bases. Thereby the area underneath the electropherogram of a detected base is calculated. The degree of methylation is then deduced by comparison this value for a cytosine position to be analyzed with the value obtained for an unmethylated cytosine. For better results, the determination and the consideration of the conversion rate of cytosine to uracil of the bisulfite treatment and/or a standardization of electropherogram signals is favorable. It is also especially preferred that the bisulfite sequencing is performed and the results analyzed as described in EP06090125.

According to a preferred embodiment, the detection method is a method of detection by means of a DNA-array. A person skilled in the art knows at lot of suitable DNA-arrays. Preferably, a DNA array comprises DNA molecules which are bound to or elsewise associated with a solid phase. The array can be characterized, for example but not limited to it, in that the DNA molecules are arranged on the solid phase in the form of a rectangular or hexagonal lattice. Thereby the solid phase is at least one phase selected from the group comprising: silicon, glass, polystyrene, aluminum, steel, iron, copper, nickel, silver, gold, nitrocellulose, or plastics such as but not limited to it nylon. But also combinations of the said materials are thinkable. For detection, the DNA hybridized on the array is labeled, preferably with a fluorescent dye. Such labelling is for example, but not limited to it, the simple attachment of Cy3 and Cy5 dyes to the 5'-OH of the DNA fragment. The detection of the fluorescence of the hybridized DNA may be carried out, for example, but not limited to it, via a confocal microscope.

According to a particular preferred embodiment, the detection method is a method of detection by means of a oligonucleotide microarray. An overview of the prior art in oligomer array manufacturing can be gathered from a special edition of Nature Genetics (Nature Genetics Supplement, Volume 21, January 1999, and from the literature cited therein).

According to a particular preferred embodiment, the detection method is a method of detection by means of a CpG-island-microarray. Thereby the immobilized or associated DNA of the array comprises sequences which were derived from CpG islands.

According to a particular preferred embodiment, the detection method is a method of detection by means of a DNA-array as essentially described in WO 99/28498, WO 01/38565, or in WO 02/18632.

According to a preferred embodiment, the detection method is a method of detection by means of restriction enzymes. A person skilled in the art is in knowledge of suitable methods.

According to a preferred embodiment, the methylation specific amplification and the detection are carried out simultaneously. Suitable methods are known to those skilled in the art. According to a particular preferred embodiment, the method for simultaneous methylation specific amplification and detection is the COBRA method. The COBRA method is a quantitative methylation method useful for determining DNA methylation levels at specific gene loci in small amounts of genomic DNA (Xiong & Laird, Nucleic Acids Res. 25:2532-2534, 1997). According to the COBRA method, restriction enzyme digestion is used to reveal methylation-dependent sequence differences in PCR products of bisulfite-treated DNA. Methylation-dependent sequence differences are first introduced into the genomic DNA by bisulfite treatment. PCR amplification of the bisulfite converted DNA is then performed using methylation unspecific primers followed by restriction endonuclease digestion, gel electrophoresis, and detection using specific, labeled hybridization probes. Methylation levels in the original DNA sample are represented by the relative amounts of digested and undigested PCR product in a linearly quantitative fashion across a wide spectrum of DNA methylation levels. Additionally, restriction enzyme digestion of PCR products amplified from bisulfite-converted DNA is also used (Sadri & Hornsby. Nucl. Acids Res. 24:5058-5059, 1996).

According to a particular preferred embodiment, the method for simultaneous methylation specific amplification and detection is a real-time PCR method. A person skilled in the art knows suitable real-time PCR methods. According to a particular preferred embodiment, the real-time PCR method is a HeavyMethyl™ method. The HeavyMethyl™ method is thereby performed as described above by means of a real-time PCR machine.

According to a particular preferred embodiment, the real-time PCR method is a MethyLight™ method. The MethyLight™ method is a high-throughput quantitative methylation method that utilizes fluorescence-based real-time PCR (TaqMan™) technology that requires no further manipulations after the PCR step (Eads et al., Cancer Res. 59:2302-2306, 1999). Briefly, the MethyLight™ process begins with a mixed sample of genomic DNA that is converted, in a bisulfite reaction, to a mixed pool of methylation-dependent sequence differences according to standard procedures. Fluorescence-based PCR is then performed either in an "unbiased" (with primers that do not overlap known CpG methylation sites) PCR reaction, or in a "biased" (with PCR primers that overlap known CpG dinucleotides) reaction. Sequence discrimination can occur either at the level of the amplification process or at the level of the fluorescence detection process, or both. The MethyLight™ method may be used as a quantitative test for methylation patterns in the genomic DNA sample, wherein sequence discrimination occurs at the level of probe hybridization. In this quantitative version, the PCR reaction provides for unbiased amplification in the presence of a fluorescent probe that overlaps a particular putative methylation site. An unbiased control for the amount of input DNA is provided by a reaction in which neither the primers, nor the probe overlie any CpG dinucleotides. Alternatively, a qualitative test for genomic methylation is achieved by probing of the biased PCR pool with either control oligonucleotides that do not "cover" known methylation sites (a fluorescence-based version of the "MSP" technique also named MSP MethyLight™ method), or with oligonucleotides covering potential methylation sites.

The MethyLight™ process can be used with a "TaqMan®" probe in the amplification process. For example, double-stranded genomic DNA is treated with bisulfite and subjected to one of two sets of PCR reactions using TaqMan® probes; e.g., with either biased primers and TaqMan® probe, or unbiased primers and TaqMan® probe. The TaqMan® probe is dual-labeled with fluorescent "reporter" and "quencher" molecules, and is designed to be specific for a relatively high GC content region so that it melts out at about 10° C. higher temperature in the PCR cycle than the forward or reverse primers. This allows the TaqMan® probe to remain fully hybridized during the PCR annealing/extension step. As the Taq polymerase enzymatically synthesizes a new strand during PCR, it will eventually reach the annealed TaqMan® probe. The Taq polymerase 5' to 3' endonuclease activity will then displace the TaqMan® probe by digesting it to release the fluorescent reporter molecule for quantitative detection of its now unquenched signal using a real-time fluorescent detection system.

Variations on the TaqMan® detection technology that are also suitable include the use of dual-probe technology (LightCycler™), fluorescent amplification primers (Sunrise™ technology), Molecular Beacon Probes (Tyagi S., and Kramer F. R., Nature Biotechnology 14, 303-308, 1996), Scorpion primers (Whitcombe et al., Nature and Biotechnology, 17, 804-807, 1999), LNA (Locked Nucleid Acid) Double-Dye Oligonucleotide probes (Exiqon A/S) or catalytic nucleic acid activities (U.S. Pat. No. 6,140,055; patent application "Verfahren zum Nachweis eines Methylierungsmusters" filed on Jul. 27, 2006 at the European Patent Organisation). All of these techniques may be adapted in a manner suitable for use with bisulfite treated DNA, and moreover in the field of methylation analysis within CpG dinucleotides.

According to a particular preferred embodiment, the real-time PCR method is the MethyLight™ ALGO™ method. The MethyLight™ ALGO™ method is an improved method of the MethyLight™ method as essentially described in EP 04090255. According to this improved method, the degree of methylation is calculated from the signal intensities of probes using different algorithms.

According to a particular preferred embodiment, the real-time PCR method is the QM method (quantitative methylation method; see above). This method is a methylation unspecific and therefore unbiased real-time PCR amplification. It is accompanied by the use of two methylation specific probes (MethyLight™) one for the methylated amplificate and a second for the unmethylated amplificate. In this way, two signals are generated which can be used a) to determine the ratio of methylated (CG) to unmethylated (TG) nucleic acids, and at the same time b) to determine the absolute amount of methylated nucleic acids. For the later, a calibration of the assay is necessary with a known amount of control DNA.

According to preferred embodiment, the method for simultaneous methylation specific amplification and detection is a Headloop PCR method. The Headloop PCR method is a suppression PCR method. It essentially carried out as described in Rand et al. (Rand et al., Nucleic Acid Research, 33(14), e127). It is a PCR method for distinguishing related sequences in which the selectivity of amplification is dependent from the amplicon's sequence. A 5' extension is included in one (or both) primer(s) that corresponds to sequences within one of the related amplicons. After copying and incorporation into the amplificate this sequence is then able to loop back, anneal to the internal sequences and prime to form a hairpin structure. This structure prevents then further amplification. Thus, amplification of sequences containing a perfect match to the 5' extension is suppressed while amplification of sequences containing mismatches or lacking the sequence is unaffected.

According to a particular preferred embodiment, the method for simultaneous methylation specific amplification and detection is a combination of the Headloop PCR method and the MethyLight™ method, also named Headloop MethyLight™ method.

According to preferred embodiment, the method for simultaneous methylation specific amplification and detection is a Scorpion™ method. This method was first described by Whitcombe et al. (Whitcombe et al.: Detection of PCR products using self-probing amplicons and fluorescence. Nat Biotechnol. 1999; 17(8):804-7; Thelwell et al.: Mode of action and application of Scorpion™ primers to mutation detection. Nucleic Acids Res. 2000 Oct. 1; 28(19):3752-61; U.S. Pat. No. 6,326,145; U.S. Pat. No. 6,365,729; US 20030087240 A1). Several embodiments of this method are known to those skilled in the art. All of these methods have the intramolecular probing in common. According to the so-called Hairloop variant, Scorpion™ primers posses a specific probe sequence at their 5' end. This sequence is present in a hairloop like configuration. A fluorescent dye and a quencher are located in spatial proximity at the end of the probing sequence. After denaturation subsequent to an amplification cycle, the probe hybridizes intramolecularly onto the elongated primer sequence of the same strand. Thereby the hairloop is opened, the dye and the quencher are separated and thus the dye's signal can be detected.

Other Scorpion™ method variants are for example the Duplex variant (Solinas et al.: Duplex Scorpion™ primers in SNP analysis and FRET applications. Nucleic Acids Res. 2001 Oct. 15; 29(20):E96), or the variants as described in U.S. Pat. No. 6,326,145 and US 20030087240. According to a particular preferred embodiment, the Scorpion™ method is a method as essentially described in WO 05/024056.

According to a particular preferred embodiment, the method for simultaneous methylation specific amplification and detection is a combination of the HeavyMethyl™ method and the Scorpion™ method, also named HeavyMethyl™ Scorpion™ method.

According to a particular preferred embodiment, the method for simultaneous methylation specific amplification and detection is a combination of the HeavyMethyl™ method and the MethyLight™ method, also named HeavyMethyl™ MethyLight™ method.

According to a particular preferred embodiment, the method for simultaneous methylation specific amplification and detection is a combination of the MSP method and the Scorpion™ method, also named MSP Scorpion™ method.

According to a particular preferred embodiment, the method for simultaneous methylation specific amplification and detection is a combination of the Headloop method and the Scorpion™ method, also named Headloop Scorpion™ method.

According to a preferred embodiment, the method for simultaneous methylation specific amplification and detection is a method of methylation specific primer extension. A person skilled in the art knows several methods which can be used according to the invention.

According to a particular preferred embodiment, the method of methylation specific primer extension is the Ms-SNuPE (methylation-sensitive Single Nucleotide Primer Extension) method. The Ms-SNuPE method is a method as essentially carried out as described in Gonzalgo et al. (Gonzalgo et al., Nucleic Acids Research 25(12), 2529-2531, 1997; U.S. Pat. No. 6,251,594). According to the Ms-SNuPE method, regions of interest are amplified by PCR from bisulfite treated DNA. After purification of the PCR products, primers are proximately hybridized in front of the position to be analyzed. The primer is then elongated by a single nucleotide either with labeled dCTP or with differently labeled dTTP. In case the cytosine in the original DNA was methylated, then dCTP will be incorporated because methylated cytosines remain unchanged during bisulfite treatment. In the other case, the cytosine in the original DNA was unmethylated, then dTTP will be incorporated because unmethylated cytosine is converted to uracil by bisulfite treatment and subsequent PCR will substitute uracil by thymine. By detection of the different labels, it can be distinguished if a cytosine of a CpG position was methylated or unmethylated. The MS-SNuPE method can also be performed in a quantitative manner.

According to a particular preferred embodiment, the method of methylation specific primer extension is a method as essentially described in WO 01/062960, WO 01/062064, or WO 01/62961. All of these methods can be performed in a quantitative manner. According to WO 01/062960, the primer to be extended hybridizes with its 3' terminus complete or only partially onto the positions of interest. An extension of at least one nucleotide occurs only if the primer hybridizes completely. WO 01/062064 discloses a method in which the primer to be extended hybridizes proximately adjacent or at a distance of up to ten bases to the position to be analyzed. The primer is then extended by at least a single nucleotide. The third method is described in WO 01/62961. According to this method, two sets of oligonucleotides are hybridized to the amplified DNA after bisulfite treatment. The first type of oligonucleotide hybridizes 5' proximately adjacent or at a distance of up to 10 bases to the position to be analyzed. The second type of oligonucleotide hybridizes on the amplified DNA so that its 5' terminus hybridizes 3' proximately adjacent to said position to be analyzed. Through this, the two oligonucleotides are separated from each other by a gap of in the range of 1 to 10 nucleotides. The first type of oligonucleotide is then extended by means of a polymerase, wherein not more than the number of nucleotides lying between the two oligonucleotides are added. Thereby nucleotides are used which comprise differentially labeled dCTP and/or dTTP. The two oligonucleotides are then linked to each other by means of a ligase enzyme. In case the cytosine in the original DNA was methylated, then dCTP will be incorporated. In case the cytosine in the original DNA was unmethylated, then dTTP will be incorporated.

Of course other similar methods, which are further developed methods of the named methods or combinations thereof are also useable according to the invention.

Most particular preferred, analyzing both of the converted nucleic acid strands comprises at least one selected from the group comprising: real-time PCR, HeavyMethyl™ real time PCR method, MSP MethyLight™ method, MethyLight™ method, MethyLight™ Algo™ method, QM method, Headloop MethyLight™ method, HeavyMethyl™ MethyLight™ method, HeavyMethyl™ Scorpion™ method, MSP Scorpion™ method, Headloop Scorpion™ method, methylation sensitive primer extension, and Ms-SNuPE (methylation-sensitive single nucleotide primer extension) method.

In a most particular preferred embodiment the analysis of the two converted nucleic acid strands comprises at least one method selected from the group comprising: real-time PCR, HeavyMethyl™ real time PCR method, MSP MethyLight™ method, MethyLight™ method, MethyLight™ Algo™ method, QM method, Headloop MethyLight™ method, HeavyMethyl™ MethyLight™ method, HeavyMethyl™ Scorpion™ method, MSP Scorpion™ method, Headloop Scorpion™ method, methylation sensitive primer extension, and Ms-SNuPE (methylation-sensitive single nucleotide primer extension) method.

In a preferred embodiment, analyzing both of the converted strands comprises the analysis of each converted strand by a reaction of the same method. A preferred embodiment comprises that both of the converted strands are analyzed by the same method.

In a preferred embodiment, analyzing both of the converted strands comprises the analysis of one converted strand by a reaction of the a method and the analyzes of the other converted strand by a reaction of a different method. A preferred embodiment comprises that one of the converted strands is analyzed by a method and that the other strand is analyzed by another method.

In a preferred embodiment, analyzing both of the converted strands comprises the analysis of each converted strand by a HeavyMethyl™ PCR reaction. In a preferred embodiment, analyzing both of the converted strands comprises the analysis of each converted strand by a real time HeavyMethyl™ PCR reaction. A preferred embodiment comprises that both of the converted strands are analyzed by the HeavyMethyl™ PCR method, preferably by the real time HeavyMethyl™ PCR method.

In a preferred embodiment, analyzing both of the converted strands comprises the analyzes of one converted strand by a HeavyMethyl™ PCR reaction and the analyzes of the other converted strand by a methylation unspecific PCR reaction. In a preferred embodiment, analyzing both of the converted strands comprises the analyzes of one converted strand by a real time HeavyMethyl™ PCR reaction and the analyzes of the other converted strand by a methylation unspecific real time PCR reaction. A preferred embodiment comprises that one of the converted strands is analyzed by the HeavyMethyl™ PCR method and that the other strand is analyzed by a methylation unspecific method, preferably the HeavyMethyl™ PCR method, the methylation unspecific method, or both are real time PCR methods.

In a preferred embodiment, analyzing both of the converted strands comprises the analyzes of each converted strand by a MSP reaction. In a preferred embodiment, analyzing both of the converted strands comprises the analyzes of each converted strand by a real time MSP reaction. A preferred embodiment comprises that both of the converted strands are analyzed by the MSP method, preferably by the real time MSP method.

In a preferred embodiment, analyzing both of the converted strands comprises the analyzes of one converted strand by a MSP reaction and the analyzes of the other converted strand by a methylation unspecific PCR reaction. In a preferred embodiment, analyzing both of the converted strands comprises the analyzes of one converted strand by a real time MSP reaction and the analyzes of the other converted strand by a methylation unspecific real time PCR reaction. A preferred embodiment comprises that one of the converted strands is analyzed by the MSP method and that the other strand is analyzed by a methylation unspecific method, preferably the MSP method, the methylation unspecific method, or both are real time PCR methods.

In a preferred embodiment, analyzing both of the converted strands comprises the analyzes of each converted strand by a MethyLight™ PCR reaction. A preferred embodiment comprises that both of the converted strands are analyzed by the MethyLight™ method.

In a preferred embodiment, analyzing both of the converted strands comprises the analyzes of one converted strand by a MethyLight™ PCR reaction and the analyzes of the other converted strand by a methylation unspecific PCR reaction. In a preferred embodiment, analyzing both of the converted strands comprises the analyzes of one converted strand by a MethyLight™ PCR reaction and the analyzes of the other converted strand by a methylation unspecific real time PCR reaction. A preferred embodiment comprises that one of the converted strands is analyzed by the MethyLight™ method and that the other strand is analyzed by a methylation unspecific method, preferably the methylation unspecific method is a real time PCR method.

In a preferred embodiment, analyzing both of the converted strands comprises the analyzes of each converted strand by a QM reaction. In a preferred embodiment, analyzing both of the converted strands comprises the analyzes of each converted strand by a real time QM reaction. A preferred embodiment comprises that both of the converted strands are analyzed by the QM method, preferably by the real time QM method.

In a preferred embodiment, analyzing both of the converted strands comprises the analyzes of one converted strand by a QM reaction and the analyzes of the other converted strand by a methylation unspecific PCR reaction. In a preferred embodiment, analyzing both of the converted strands comprises the analyzes of one converted strand by a real time QM reaction and the analyzes of the other converted strand by a methylation unspecific real time PCR reaction. A preferred embodiment comprises that one of the converted strands is analyzed by the QM method and that the other strand is analyzed by a methylation unspecific method, preferably the QM method, the methylation unspecific method, or both are real time PCR methods.

A preferred embodiment comprises the analysis of one converted strand by a HeavyMethyl™ method reaction and the analysis of the other converted strand by a MSP method reaction. Preferably, the HeavyMethyl™ method reaction, the MSP method reaction, or both are real time reactions.

A preferred embodiment comprises the analysis of one converted strand by a HeavyMethyl™ method reaction and the analysis of the other converted strand by a QM method reaction. Preferably, the HeavyMethyl™ method reaction, the QM method reaction, or both are real time reactions.

A preferred embodiment comprises the analysis of one converted strand by a MSP method reaction and the analysis of the other converted strand by a QM method reaction. Preferably, the MSP method reaction, the QM method reaction, or both are real time reactions.

A preferred embodiment comprises the analysis of one converted strand by either a HeavyMethyl™ method reaction, a MSP method reaction or a QM method reaction and the analysis of the other converted strand by a MethyLight™ method reaction. Preferably, the HeavyMethyl™ method reaction, the MSP method reaction and the QM method reaction is a real time reaction, respectively.

A preferred embodiment is a method for methylation analysis, comprising
 providing double stranded nucleic acid;
 converting one of the two provided nucleic acid strands in such a way that 5-methylcytosine remains unchanged, while unmethylated cytosine is converted to uracil or to another base that is distinguished by cytosine in its base-pairing behavior, said reaction leading to two different nucleic acid strands that are no longer complementary to each other;
 analyzing both of the nucleic acid strands, wherein the converted strand is analyzed in a methylation specific reaction and the other unconverted strand is analyzed in a methylation unspecific reaction. Preferably, the methylation unspecific reaction comprises the analysis of SNP, deletion or amplification of adjacent one or more nucleotides, or copy number. Preferably, the converting of one of the two provided nucleic acid strands comprises a bisulfite reagent. Preferably, the methylation specific analysis comprises the analysis of one or more CpG positions located on the converted strand and the analysis of a corresponding, overlapping, adjacent or different section located on the other unconverted strand. Preferably, analyzing both of the strands comprises the quantification of one or more methylation pattern, the quantification of converted nucleic acid strands, the quantification of unconverted nucleic acids strands, or combinations thereof. Preferably, analyzing both of the strands comprises at least one selected from the group comprising: amplification method, PCR method, isothermal amplification method, NASBA method, LCR method, methylation specific amplification method, MSP (Methylation Specific PCR) method, nested MSP method, HeavyMethyl™ method, detection method, methylation specific detection method, bisulfite sequencing method, detection by means of microarrays, detection by means of oligonucleotide microarrays, detection by means of restriction enzymes, simultaneous methylation specific amplification and detection method, real-time PCR, HeavyMethyl™ real time PCR method, MSP MethyLight™ method, MethyLight™ method, MethyLight™ Algo™ method, QM method, Headloop MethyLight™ method, HeavyMethyl™ MethyLight™ method, HeavyMethyl™ Scorpion™ method, MSP Scorpion™ method, Headloop Scorpion™ method, methylation sensitive primer extension, and Ms-SNuPE (methylation-sensitive Single nucleotide primer extension) method.

In a preferred embodiment, genomic DNA is analyzed, said genomic DNA comprises at least one cytosine that is methylated in the range of 0-100%.

In a preferred embodiment, genomic DNA is analyzed, said genomic DNA comprising a cytosine which is methylated to about 0%, 0.1%, 0.2%, 0.3%, 0.4%, 0.5%, 0.6%, 0.7%, 0.8%, 0.9%, 1.0%, 2.0%, 3.0%, 4.0%, 5.0%, 6.0%, 7.0%, 8.0%, 9.0%, 10.0%, 12.0%, 88.0%, 90.0%, 91.0%, 92.0%, 93.0%, 94.0%, 95.0%, 96.0%, 97.0%, 98.0%, 99.0%, 99.1%, 99.2%, 99.3%, 99.4%, 99.5%, 99.6%, 99.7%, 99.8%, 99.9%, or 100.0%.

In a preferred embodiment, genomic DNA is analyzed by real time PCR.

A preferred embodiment is a method for diagnosis of cancer, comprising the use of the method of the invention for determining the methylation status of a CpG position of the gene TMEFF 2 and/or a regulatory region thereof, wherein the presence of CpG methylation is indicative for the presence of cancer. In a preferred embodiment, the method of the invention is a method for diagnosis of cancer. It comprises providing double stranded nucleic acid; converting said nucleic acid in such a way that 5-methylcytosine remains unchanged, while unmethylated cytosine is converted to uracil or to another base that is distinguished by cytosine in its base-pairing behavior, said reaction leading to two different converted nucleic acid strands that are no longer complementary to each other; and analyzing both of the converted nucleic acid strands, wherein at least one of the both strands in analyzed in a methylation specific reaction. Thereby the methylation of cytosine of a CpG position of the gene TMEFF 2 or of a regulatory region thereof is determined i.e. the presence or absence of cytosine methylation and/or the degree of methylation or unmethylation are determined. The presence of cytosine methylation or the presence of a partial cytosine methylation is then indicative for the presence of cancer.

Kit.

Aspects of the present invention relate to a kit comprising a container, one or more primers, and an enzyme or reagent for conversion of nucleic acid. Aspects of the present invention relate to a kit comprising a container, a bisulfite reagent or an cytidin-deaminase, and four or more primers. Preferably said kit comprises in addition one, two or more probes; one, two, or more blocker molecules; or both.

A kit of the invention is a kit for performing one or more embodiments of the method of the invention. Said kit comprises a container, one or more primers, an enzyme or reagent for conversion of a nucleic acid. Preferably, said kit comprises at least one probe, at least one blocker, or both. A more preferred kit, comprises a container, 1, 2, 3, 4, 5, 6, 7, 8, or more primers, a bisulfite reagent and/or a cytidin-deaminase, 1, 2, 3, 4 or more probes, and 1, 2, 3, 4 or more blockers an enzyme or reagent for conversion of a nucleic acid A kit of the invention comprises a container, four primers, and an enzyme or reagent for conversion of nucleic acid. Preferably, said enzyme is a cytidin-deaminase. Preferably, said reagent is a bisulfite reagent. Preferably, said one or more primers are 1, 2, 3, 4, 5, 6, 7, 8, or more primers.

A preferred kit additional comprises 1, 2, or more probes; 1, 2, or more blockers; or combinations thereof.

A preferred kit also comprises one or more additional reagents, devices or enzymes necessary or useful for performing a PCR reaction of the methods described herein or for performing a nucleic acid conversion described herein. Preferably, such one or more additional reagents, devices or enzymes are reagents, devices or enzymes necessary or useful for performing a real time PCR method; for performing a bisulfite conversion; or both.

A person skilled in the art knows such additional reagents, devices or enzymes.

A preferred kit is also a kit, wherein the one or more primers comprise two pairs of primers, wherein one pair is respectively specific for one of the two strands of the provided double stranded nucleic acid. In a preferred kit, the one or more primers comprise two primers, wherein one of the said primers is specific for one of the two strands of the provided double stranded nucleic acid, and wherein the other of the said primers is specific for the other of the two strands of the provided double stranded nucleic acid. A particular preferred kit comprises two or more primers, wherein one of the said primers is specific for one converted strand of the provided double stranded nucleic acid, and wherein the other is specific for the other converted strand of the provided double stranded nucleic acid.

Use of a Method or a Kit of the Invention.

Particular aspects of the invention relate to the use of the method of the invention or to the use of a kit of the invention. In particular, the use of a method or kit of the invention is preferred for at least one of the following with regard to a patient or individual: diagnosing a condition, prognosing a condition, predicting a treatment response, diagnosing a predisposition for a condition, diagnosing a progression of a condition, grading a condition, staging a condition, classification of a condition, characterization of a condition, or combinations thereof, wherein the condition is a healthy condition or an adverse event, the adverse event comprises at least one category selected from the group comprising: undesired drug interactions; cancer diseases, proliferative diseases or therewith associated diseases; CNS malfunctions; damage or disease; symptoms of aggression or behavioral disturbances; clinical; psychological and social consequences of brain damages; psychotic disturbances and personality disorders; dementia and/or associated syndromes; cardiovascular disease of the gastrointestinal tract; malfunction, damage or disease of the respiratory system; lesion, inflammation, infection, immunity and/or convalescence; malfunction, damage or disease of the body as an abnormality in the development process; malfunction, damage or disease of the skin, of the muscles, of the connective tissue or of the bones; endocrine and metabolic malfunction, damage or disease; and headaches or sexual malfunction. Accordingly a nucleic acid is obtained from a sample derived from an individual or patient. Said nucleic acid is then analyzed according to the method of the invention. Preferably, therefore a kit of the invention is used. The results obtained by this analysis enable then the said diagnosing a condition, prognosing a condition, predicting a treatment response, diagnosing a predisposition for a condition, diagnosing a progression of a condition, grading a condition, staging a condition, classification of a condition, characterization of a condition, or combinations thereof.

In particular, the use of a method or kit of the invention is preferred for distinguishing cell types or tissue, or for investigating cell differentiation. Accordingly a nucleic acid is obtained ex vivo from samples of cells, cell types or tissue. Said nucleic acid is then analyzed according to the method of the invention. Preferably, therefore a kit of the invention is used. The results obtained by this analysis characterized the cells, cell types or tissue. Therewith the results enable the distinguishing of cell types or tissue, or the investigating of cell differentiation.

All herein cited documents are incorporated by reference to their entirety.

BRIEF DESCRIPTION OF THE FIGURES

FIG. 2 gives an overview of the HQM assay design as well the QM assay design of Example 1. The HQM assay has a HM reaction specific for unmethylation (a), wherein the upper bisulfite converted DNA strand of the TMEFF2 gene is used. Underneath the sequences of the used primers, the blocker and the probe is given. The HQM assay has a HM reaction specific for methylation (b), wherein the lower bisulfite converted DNA strand of the TMEFF2 gene is used. Underneath the used sequences of the primers, the blocker and the probe is given. The QM assay is specific for methylation and unmethylation, wherein the lower bisulfite converted DNA strand of the TMEFF2 gene is used. Underneath the used sequences of the primers and probes is given. The sequences or the reverse complementary sequences of the primers, blockers and probes are indicated in the shown sequences: once underlined=respective forward primer; twice underlined=respective reverse primer, in fat letters=respective blocker, italicized=respective probes, grey highlighted=nucleotides of CpG positions or nucleotides of primers, blockers or probes corresponding to CpG positions.

DEFINITIONS

Figure 1:
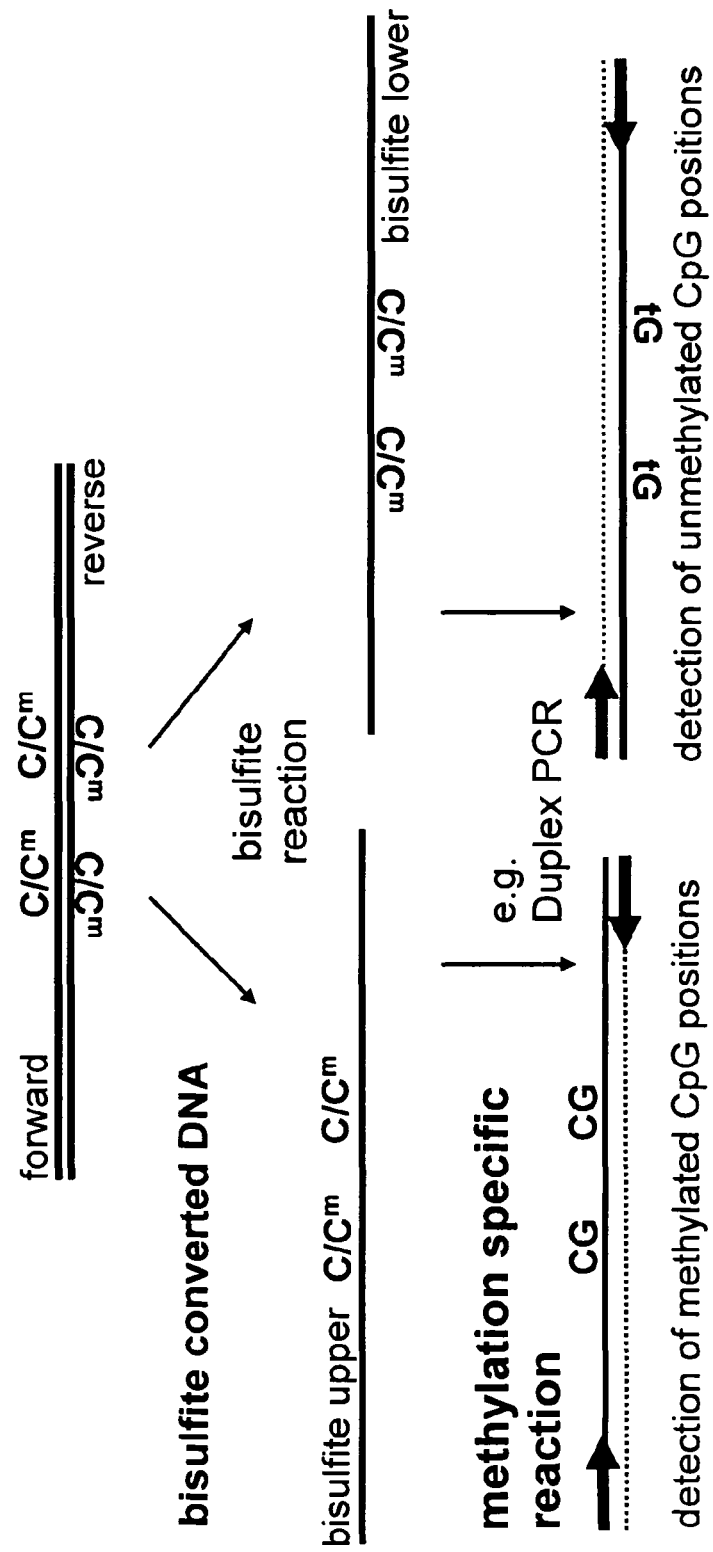
FIG. 1 shows an overview of one embodiment, wherein genomic DNA is converted by means of bisulfite. The resulting two converted strands bisulfite upper and bisulfite lower are then analyzed respectively in a methylation specific reaction. Thereby one bisulfite converted strand is analyzed with respect to the presence of methylation of one or more CpG positions, while the other converted strand is analyzed with respect to the absence of methylation of the same one or more CpG positions.
Figure 3A:
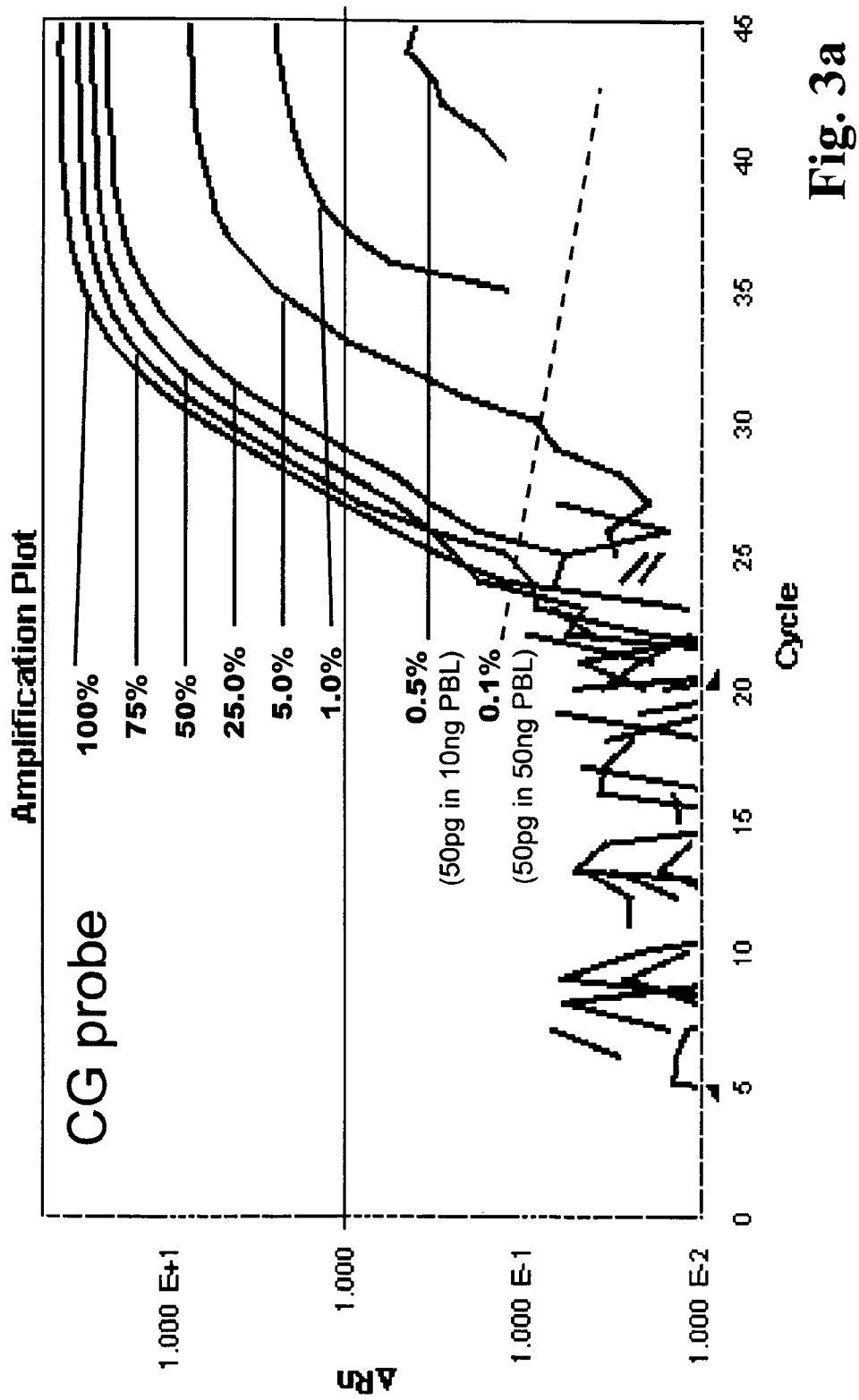
FIG. 3 shows the results of the QM experiment of Experiment 1. The QM assay performs well comparable to other QM assays, because it is able to detect 1% methylation. The Figure shows the amplifications plots of the CG-probe (methylation specific probe) and of the tG-probe (non-methylation specific probe). Each plot shows the amplification curves of the applied bisulfite converted differentially methylated DNA.
Figure 3B:
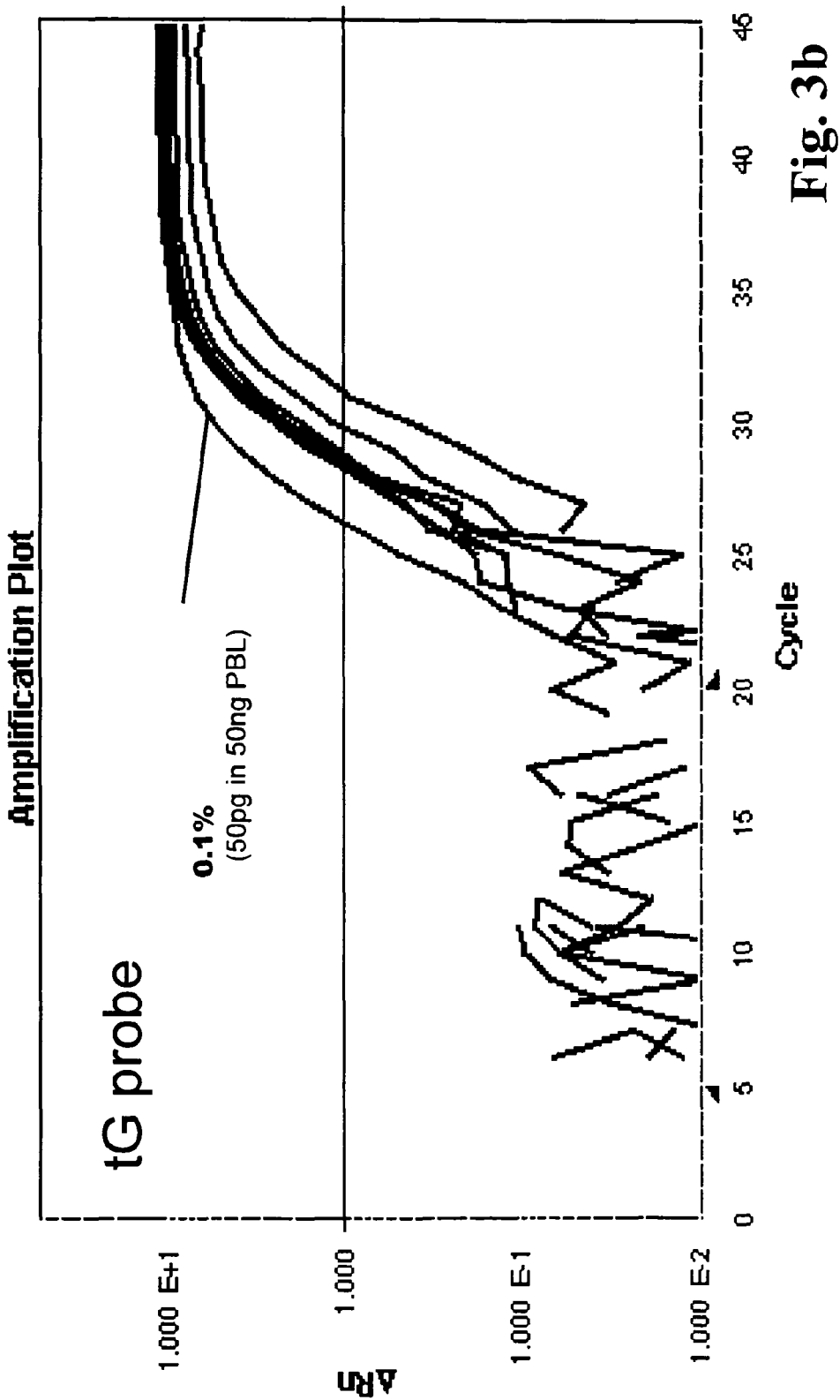
Figure 4A:
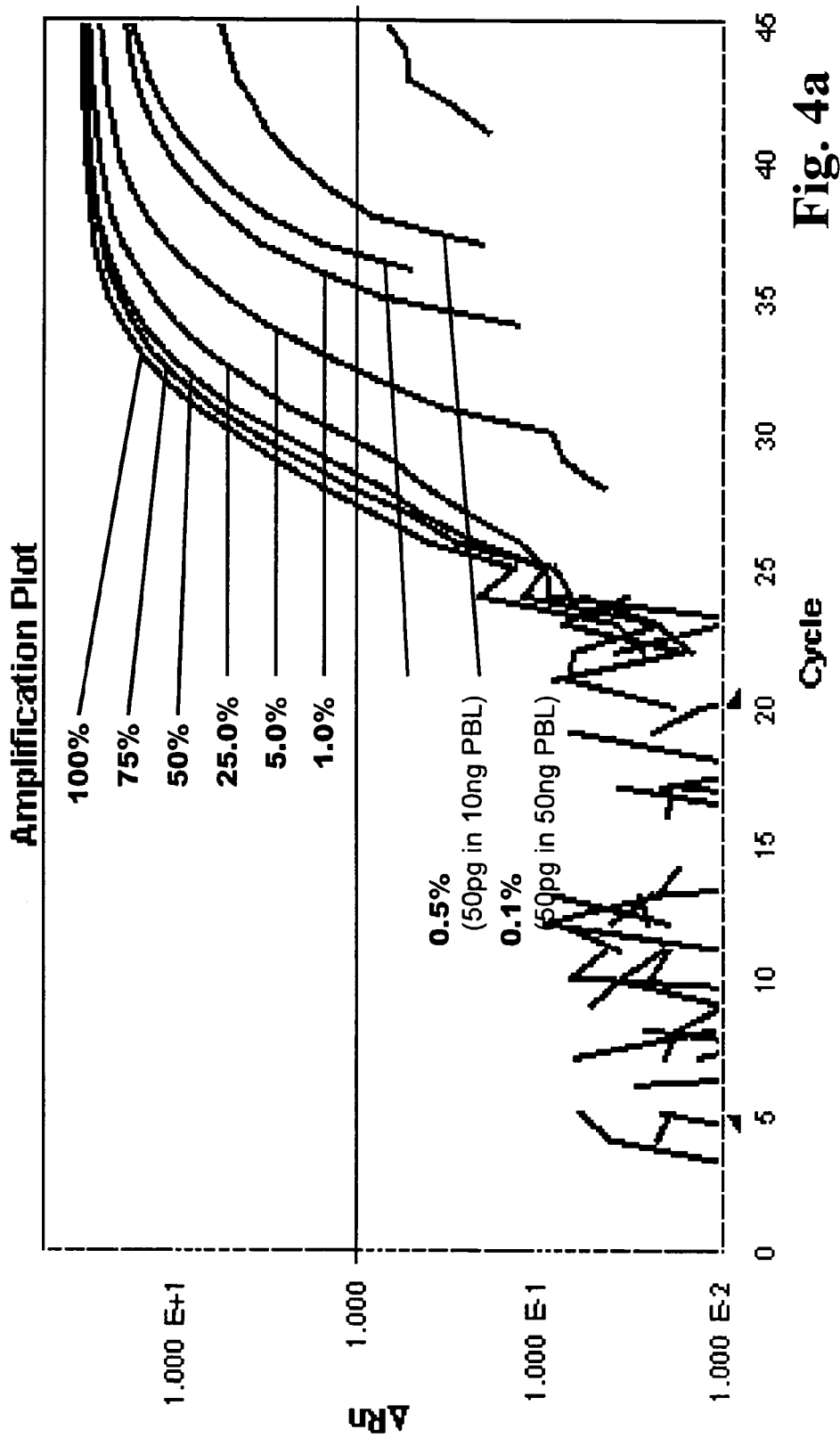
FIG. 4 shows the results of the HQM experiment of Experiment 1. The HQM assay performs significantly better than the QM assay. It is able to detect 0.1% methylation. It has a relative sensitivity of 1:1000. The Figure shows the amplifications plots of the CG-probe (methylation specific probe) and of the tG-probe (non-methylation specific probe). Each plot shows the amplification curves of the applied bisulfite converted differentially methylated DNA.
Figure 4B:
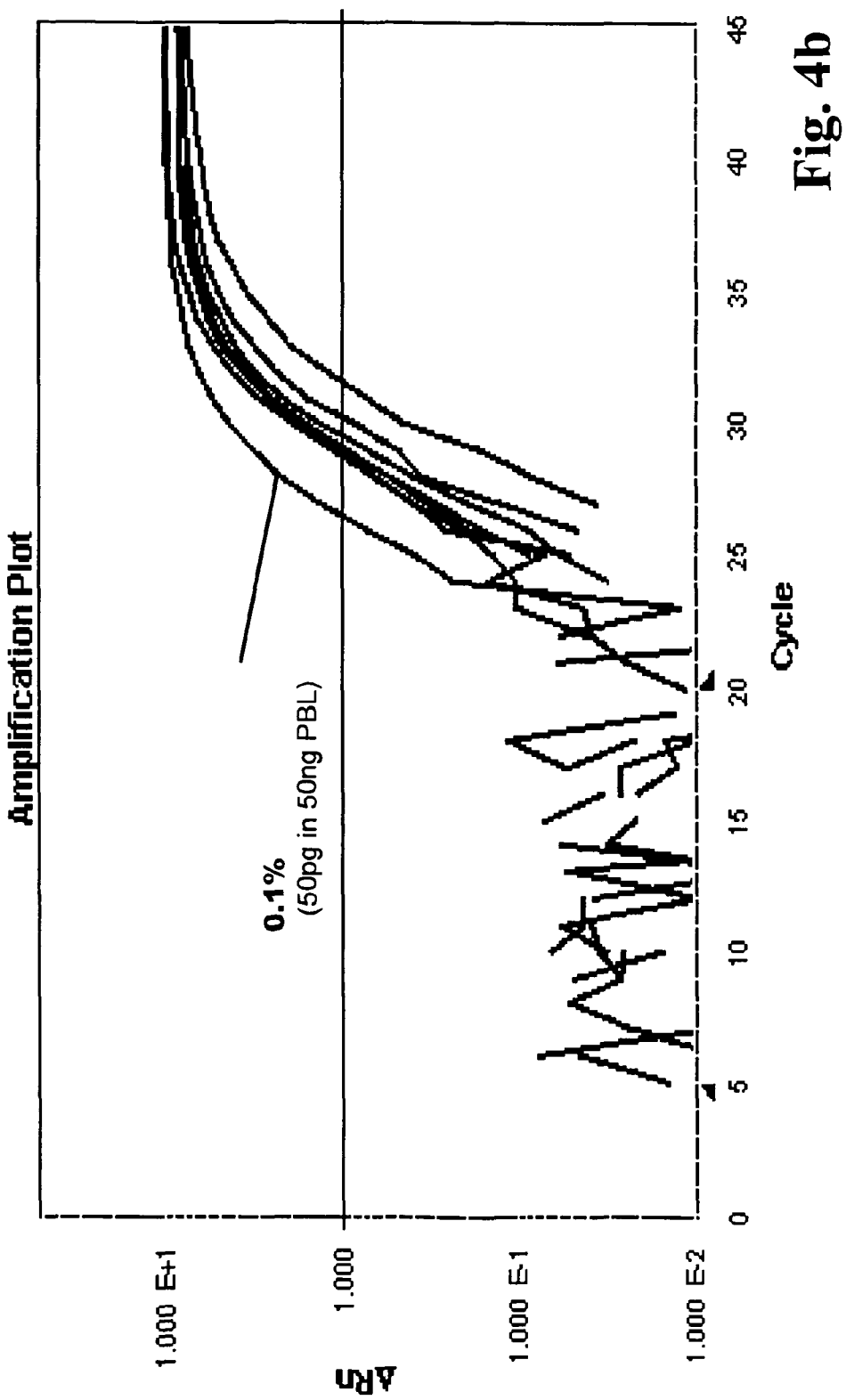
Figure 5A:
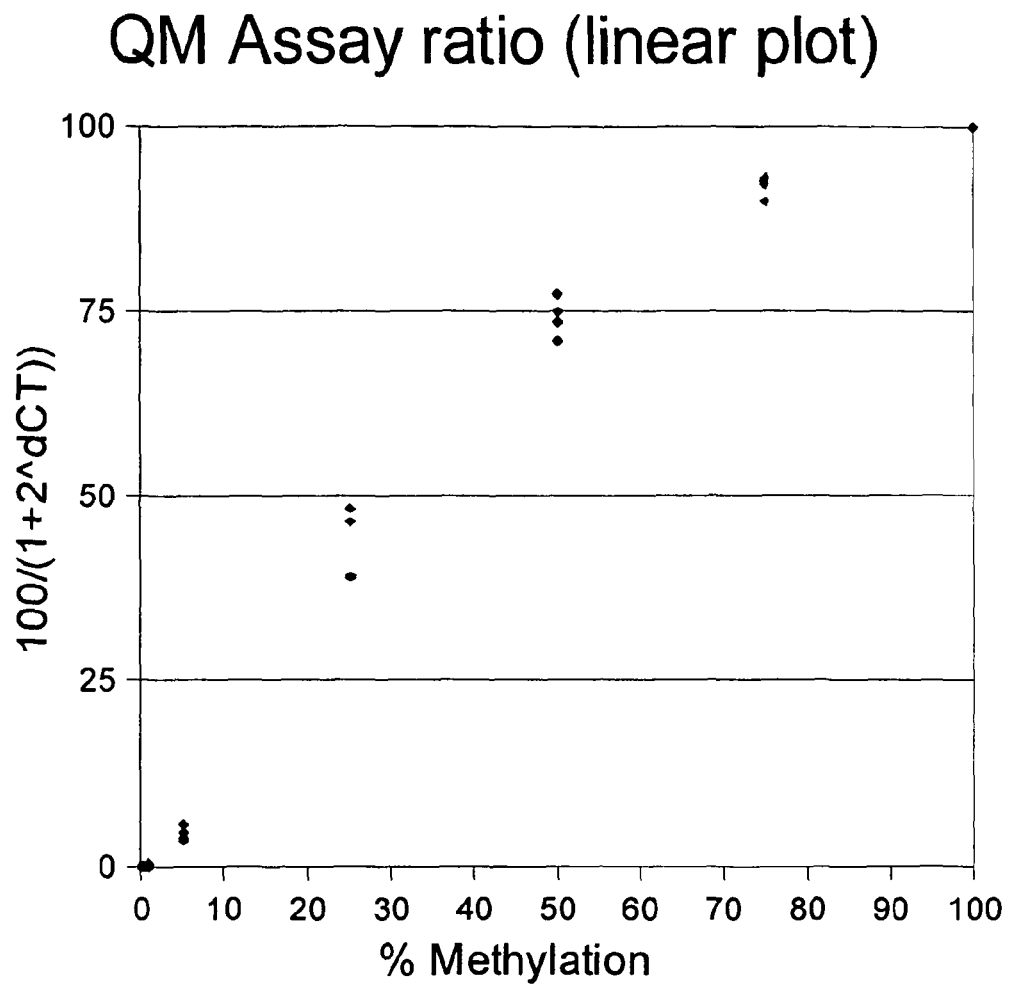
FIG. 5 shows a comparison of the QM and the HQM assay (linear plots) of Experiment 1. It also gives the median ratio of the Ct values (median ratio CT), standard deviation of the ratio of the Ct values (SD ratio CT) as well as the corresponding fisher scores (fisher score) with respect to the degree of methylation of the applied DNA. The fisher scores of the HQM assay are higher then the fisher scores of the QM method this means that the HQM assay has a better reproducability.
Figure 5B:
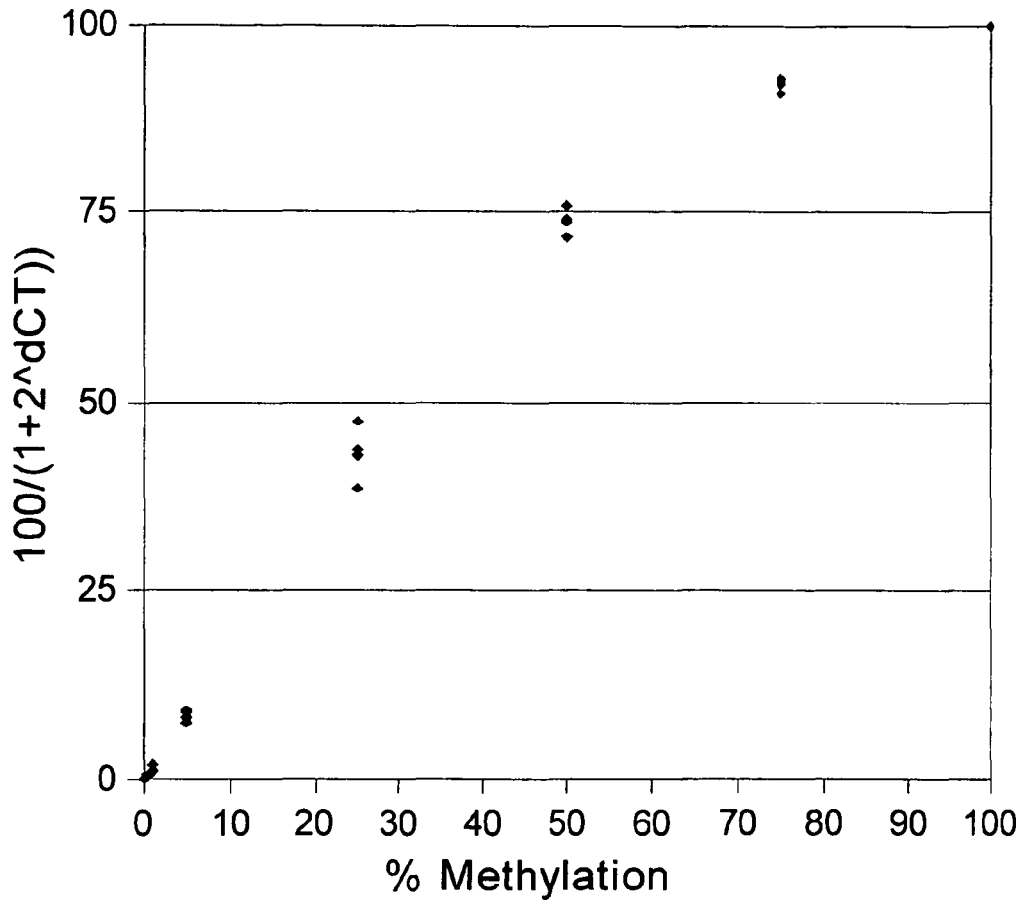
Figure 6A:
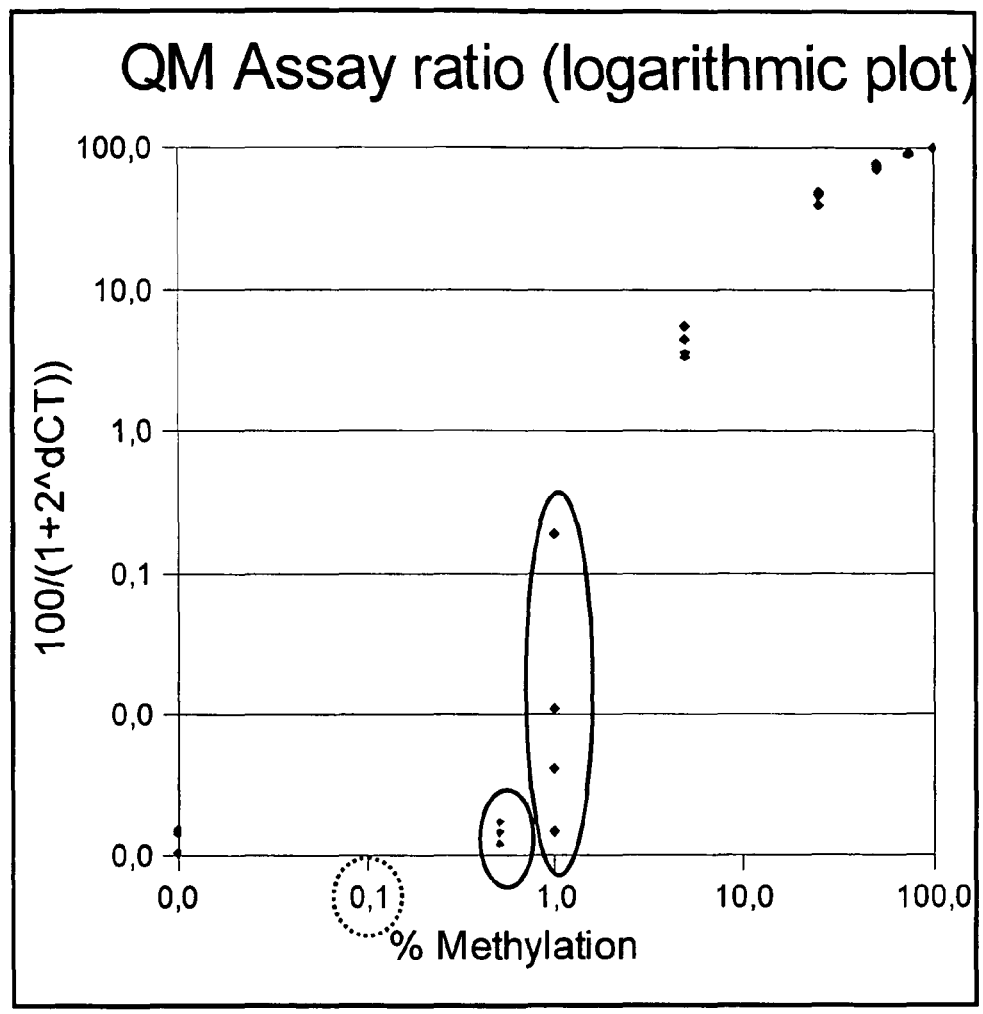
FIG. 6 shows a comparison of the QM and the HQM assay (logarithmic plots). It also gives the median ratio of the Ct values (median ratio CT), standard deviation of the ratio of the Ct values (SD ratio CT) as well as the corresponding fisher scores (fisher score) with respect to the degree of methylation of the applied DNA. The fisher scores of the HQM assay are higher then the fisher scores of the QM method this means that the HQM assay has a better reproducability. The HQM assay in contrast to the QM assay is able to differentiate between 0% and 0.1% methylation and to differentiate between 0.5% to 1.0% methylation.
Figure 6B:
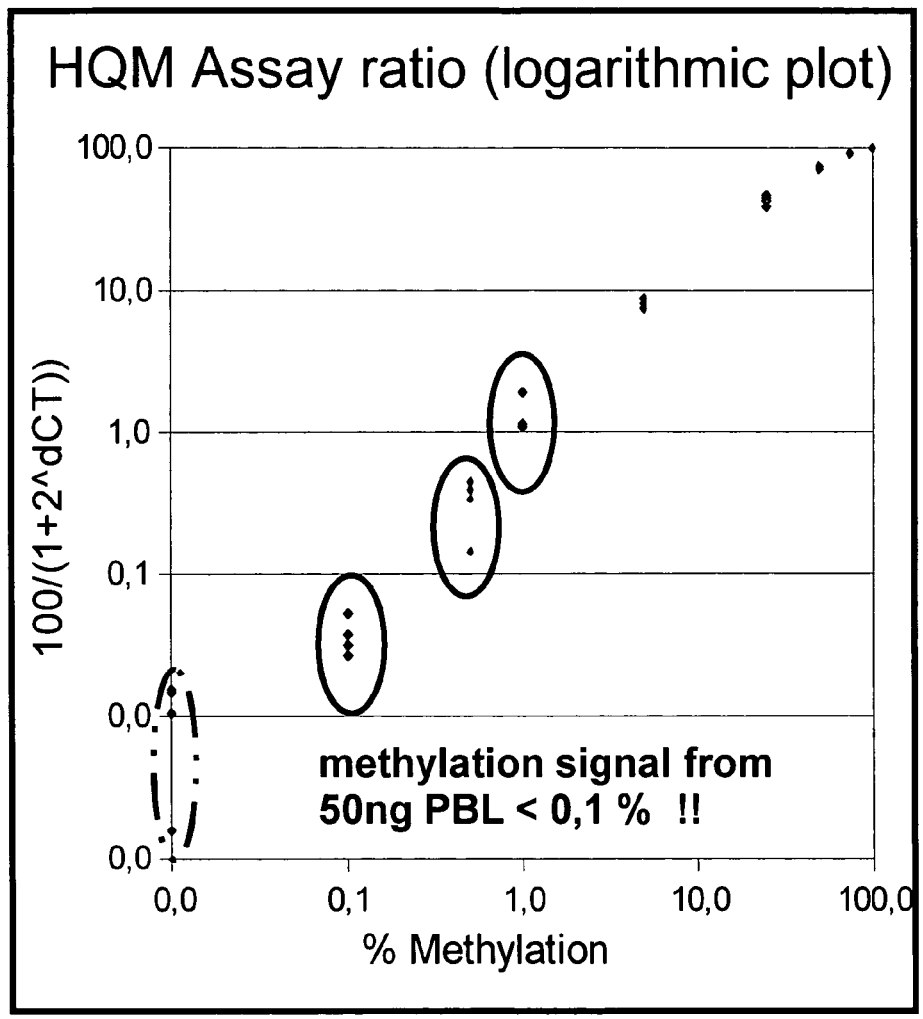

In particular aspects, the term "methylation pattern" refers to, but is not limited to, the presence or absence of methylation of one or more nucleotides. Thereby said one or more nucleotides are comprised in a single nucleic acid molecule. They have the ability of being methylated or being non-methylated. The term "methylation status" can also be used, but is not limited to, wherein only a single nucleotide is considered. A methylation pattern can be quantified, wherein it is considered over more than one nucleic acid.

In particular aspects, the term "methylation status" refers to, but is not limited to, the presence or absence of methylation of one nucleotide. Thereby said nucleotide has the ability of being methylated or being non-methylated. A methylation status can be quantified, wherein a it is considered over more than one nucleic acid.

In particular aspects, the term "sensitivity" refers to, but is not limited to, the measure of a method's or in particular of a PCR's ability to correctly detect an event or a condition, in particular the presence or absence of methylation. A method or PCR having poor sensitivity produces a high rate of false negatives. For example, the presence or absence of methylation is indicative for a disease. False negatives lead then to the situation wherein individuals who have said disease are falsely identified as being free of that particular disease. The potential danger of a false negative result is that the diseased individual will remain undiagnosed and untreated for some period of time, during which the disease may progress to a later stage wherein treatments, if any, may be less effective. Mathematical, sensitivity can be described as: Sensitivity=TP/(TP+FN). Thereby TP represents a true positive result and FN a false negative result. A true positive result means that the outcome of the method is indicative for the presence of a condition and the condition is present. A false negative result is where the outcome of the method is indicative for the absence of a condition and the condition is not present.

In particular aspects, the term "specificity" refers to, but is not limited to, the measure of a method's or in particular of a PCR's ability to identify accurately the presence of an event or a condition, in particular the presence or absence of methylation. A method or PCR having poor specificity produces a high rate of false positives. For example, the presence (or absence) of methylation is indicative for a disease. False positive results lead then to the situation, wherein healthy individuals are falsely identified as having the disease. A drawback of false positive results is that they force patients to undergo unnecessary medical procedures or treatments with their attendant risks, emotional and financial stresses, and which could have adverse effects on the patient's health. Mathematical, specificity can be described as: Specificity=TN/(FP+TN). Thereby TN represents a true negative result and FP a false positive result. A true negative result is where the outcome of a method is negative and the condition is not present. A false positive result is where the outcome of a method is positive but the condition is not present.

In particular aspects, the term "methylation specific" refers to, but is not limited to, the dependency from the presence or absence of methylation. The term "methylation specific" is the opposite of the term "non-methylation specific" or the term "methylation unspecific".

In particular aspects, the term "non-methylation specific" or "methylation unspecific" refers to, but is not limited to, the independency from the presence or absence of methylation. The term "non-methylation specific" or the term "methylation unspecific" is the opposite of the term "methylation specific".

In particular aspects, the term "CpG dinucleotide" refers to, but is not limited to, the sequence 5'-CG-3' in a nucleic acid, in particular in a DNA, RNA, or PNA, and most particular in a genomic DNA.

In particular aspects, the term "CpG position" refers to, but is not limited to, a site in a double stranded nucleic acid, wherein a CpG dinculeotide is present on one strand and another reverse complementary CpG dinucleotide is present on the other reverse complementary strand.

In particular aspects, the term "methylation analysis" refers to, but is not limited to, the analysis of the presence or absence of one or more methylation pattern. Synonymously, it refers to, but is not limited to, the analysis of the presence of absence of methylation of one or more cytosines.

In particular aspects, the term "corresponding sections" refers to, but is not limited to, two sections, one on each strand, wherein both sections are reverse complementary to one another before conversion. But they are no longer reverse complementary after conversion.

In particular aspects, the term "overlapping sections" refers to, but is not limited to, two sections, one on each strand, wherein both sections are partially reverse complementary to one another before conversion. But they are no longer reverse complementary after conversion.

In particular aspects, the term "adjacent sections" refers to, but is not limited to, two sections, one on each strand, wherein one section is reverse complementary to a section on the respective other strand, whereby said reverse complementary section is immediately located before or after the other considered section. Adjacent sections are neither before nor after conversion reverse complementary to one another.

In particular aspects, the term "different sections" refers to, but is not limited to, two sections, one on each strand, wherein both sections are not reverse complementary to one another before conversion and wherein the reverse complementary section of one section is not immediately located before or after the other considered section. Different sections are neither before nor after conversion reverse complementary to one another.

The term "HQM" refers herein to a particular preferred embodiment of the invention. Thereby "HQM" stands for Heavy Quantitative Methylation Assay.

EXAMPLES

Example 1

Comparison of the HQM Method with the QM Method

QM method: The QM method has a relative good quantitative performance due to an internal calibration. Thereby the method uses the ratio of the signal of the probe specific for methylated DNA to the signal of the probe specific for unmethylated DNA. The disadvantage of the QM method is that it has a limited sensitivity. This is based therein i) that the amplification is methylation unspecific; ii) that the signal specific for methylated DNA decreases with the presence of a large increasing portion of unmethylated DNA; and iii) that the signal specific for unmethylated DNA decreases with the presence of a large increasing portion of methylated DNA. Therefore the method has poor error associated resolution when analysing a sample with less than 10% methylated DNA (90% unmethylation) or when analyzing a sample with higher than 90% methylated DNA (10% unmethylation). Values smaller than 1% methylation (99% unmethylation) or larger than 99% methylation (1% unmethylation) are not correctly and reliably detectable.

HQM method: The HQM method comprises for example, but is not limited to, two HM reactions combined into a single reaction. In the HM reaction A methylated DNA of a region of interest is amplified. The amplification is detected in the fluorescence chanal A. In the HM reaction B unmethylated DNA of the same region of interest is amplified. The amplification is detected in the fluorescence chanal B. The two HM reactions are realized in parallel by the use of both of the converted DNA strands. Reaction A on the converted lower strand and reaction B on the converted upper strand, or vice versa. Thereby both reactions cover the same genomic region of interest and are therefore based on the same methylation information. The blocker for enrichment of methylated DNA of the HM reaction A is located on the identical CpG positions as the blocker for enrichment of unmethylated DNA of the HM reaction B. Thereby the preferred blocker design with the best discrimination properties is usable in both HM reactions. This means that a blocking of the cytosine rich primer is preferred for the amplification of methylated DNA, because it is particularly effective. On the other hand, a blocking of the guanin rich primer is preferred for the amplification of unmethylated DNA, because it is particularly effective. In both cases the energetically strongest mismatch (cytosine/adenin mismatch) is used for the prevention of binding of the blocker onto the respectively desired amplificate. Preferably the probes for detection cover also the same CpG positions. Also in this case the probes are designable in the most specific manner, wherein a cytosine/adenin mismatch is used, the one with the strongest energetic difference. This is an additional advantage in comparison to the QM method, wherein one probe has to be comparable more unspecific. This is because, the discrimination is based on the energetically smaller difference of a thymin/guanin mismatch.

Results of the HQM method are obtainable according to at least one of the two algorithms:
A) Determination of the concentration of methylated DNA as well as the determination of the concentration of unmethylated DNA by means of the use of a dilution serie of a standard. Preferably, such a standard is 50% methylated DNA. It can be used simultaneously for both HM reactions.

B) Direkt generation of the ratio of the Ct values (threshold cycles also known as crossing points). In addition, it is preferred to calibrate with 50% methylated DNA.

It is ensured that sufficient PCR components are present for both reactions, irrespective when the two HM reactions of the HQM reaction reaches respectively their maximum of amplification.

Advantages of HQM method: A HQM method is based on two independent reactions. In this case, it is based on two independent HM reactions. Both of which are highly sensitive because they amplify methylation specifically. This has the advantage that the generated signals are independent from the mixing ratio of methylated and unmethylated DNA. Because of this a much higher sensitivity is reached by a HQM reaction in comparison to a QM reaction. In addition, because of this a much higher accuracy is achieved by a HQM reaction as by a single HM reaction of a conventional HM method.

Because the HQM method is based on two completely independent reactions, the obtained signals are unambiguous. Even steep amplification signal curves (slopes) are obtained at very low mixing ratios, up to 1:1000, of methylated to unmethylated DNA or of unmethylated to methylated DNA. The determination of the Ct values is therefore more accurate. It is not distorted by a to small slope. This has the effect of a higher resolution and higher accuracy of the HQM method is comparison to the QM method. [included at the end of the embodiments sections]

A QM experiment and a HQM experiment were performed for the analysis of a genomic region of the gene TMEFF2 also known as TPEF. Both experiments were run in parallel and repeated four times. The same reagents, enzymes and mixtures of methylated and unmethylated DNA were used for each method. The following Table 1 gives an overview of the applied DNA.

TABLE 1

Overview of the applied amount of bisulfite converted DNA per QM or HQM reaction.

| methyl. bis-DNA ng/PCR | unmethyl. bis-DNA ng/PCR | total bis-DNA ng/PCR | M % |
|---|---|---|---|
| 0.00 | 10.00 | 10.00 | 0.0 |
| 0.05 | 0.95 | 10.00 | 0.2 |
| 0.05 | 49.00 | 50.00 | 0.1 |
| 0.10 | 9.90 | 10.00 | 1.0 |
| 0.50 | 9.50 | 10.00 | 10.0 |
| 2.50 | 7.50 | 10.00 | 25.0 |
| 5.00 | 5.00 | 10.00 | 50.0 |
| 7.50 | 2.50 | 10.00 | 75.0 |
| 10.00 | 0.00 | 10.00 | 100.0 |

Table 2 gives an overview of the used primers, blockers and probes of the HQM experiment.

TABLE 2

Overview of the used primers, blockers and probes, their SEQ ID NOs and their sequence of the HQM experiment.

| | | |
|---|---|---|
| forward primer A | SEQ ID NO: 1 | aaaaaaaaaaaactcctctacatac |
| reverse primer A | SEQ ID NO: 2 | ggttattgtttgggttaataaatg |
| blocker A | SEQ ID NO: 3 | aCATACaCCaCaaaTaaaTTaCCaaaAaCATCaaCCaa-PH |
| probe A | SEQ ID NO: 4 | FAM-ttCGgaCGtCGttgttCGg-BHQ |
| forward primer B | SEQ ID NO: 5 | gaaagagaaaggttttttttgtatac |
| reverse primer B | SEQ ID NO: 6 | aatcactacctaaaccaacaaata |
| blocker B | SEQ ID NO: 7 | tgtataCGtCGCGggtgggttgtCGg-PH |
| probe B | SEQ ID NO: 8 | HEX-cttcccaaacaccactacccaa-BHQ |

Each HQM reaction mix (20 μl) had the following components:

| Water | | 1.2 μl |
|---|---|---|
| MgCl2 | 3.5 mmol/l | 2.0 μl |
| forward primer A | 0.30 μmol/l | 0.6 μl |
| reverse primer A | 0.30 μmol/l | 0.6 μl |
| blocker A | 4.00 μmol/l | 0.8 μl |
| probe A | 0.20 μmol/l | 0.4 μl |
| forward primer B | 0.30 μmol/l | 0.6 μl |
| reverse primer B | 0.30 μmol/l | 0.6 μl |
| blocker B | 4.00 μmol/l | 0.8 μl |
| probe B | 0.20 μmol/l | 0.4 μl |
| 10x reagent mix | | 2.0 μl |
| DNA (see Table 1) | | 10.0 μl |

The 10× reagent mix of the FastStart Kit (Roche) was used. The HQM experiment was runned on a ABI 7900 PCR machine with the following temperature program: 95° C. 10 min, 45 cycles of 95° C. 15 s (ramping rate 2° C./s), 56° C. 30 s (ramping rate 2° C./s) (detection point), 72° C. 30 s (ramping rate 2° C./s).

Table 3 gives an overview of the used primers, blockers and probes of the QM experiment.

TABLE 3

Overview of the used primers, blockers and probes, their SEQ ID NOs and their sequence Of the QM experiment.

| | | |
|---|---|---|
| forward primer A | SEQ ID NO: 1 | aaaaaaaaaaaactcctctacatac |
| reverse primer A | SEQ ID NO: 2 | ggttattgtttgggttaataaatg |
| probe A | SEQ ID NO: 4 | FAM-ttCGgaCGtCGttgttCGg-BHQ |
| probe C | SEQ ID NO: 9 | HEX-tcaaccaaacaacaacatccaa-BHQ |

Each QM reaction mix (20 μl) had the following components:

| | | |
|---|---|---|
| Water | | 2.8 μl |
| MgCl2 | 3.5 mmol/l | 2.0 μl |
| forward primer A | 0.30 μmol/l | 0.6 μl |
| reverse primer A | 0.30 μmol/l | 0.6 μl |
| probe A | 0.20 μmol/l | 0.4 μl |
| probe C | 0.20 μmol/l | 0.4 μl |
| 10x reagent mix | | 2.0 μl |
| DNA (see Table 1) | | 10.0 μl |

The 10× reagent mix of the FastStart Kit (Roche) was used. The QM experiment was runned on a ABI 7900 PCR machine with the following temperature program: 95° C. 10 min, 45 cycles of 95° C. 15 s (ramping rate 2° C./s), 56° C. 30 s (ramping rate 2° C./s) (detection point), 72° C. 30 s (ramping rate 2° C./s).

Results: In contrast to the QM assay the HQM assay is able to differentiate between 0% and 0.1% methylation, between 0.1% and 0.5%, and between 0.5% and 1% methylation. The results of the HQM assay are further characterized by higher fisher scores than the results of the QM assay. This means that the HQM assay has a better reproducability than the QM assay i.e. it is has a better reliability. In addition, the HQM assay has a sensitivity of 1:1000.

The HQM method has amongst others the advantages that: (i) the same sequence or genomic region of interest is useable as a marker and as reference; (ii) copy numbers and polymorphism of the regions of interest are simultanously detectable; (iii) signals of low methylation levels (<10%) or high methylation levels (>90%) have a good quality (correct calling of Ct values; higher precision of Ct ratios (fisher scores)); (iv) saves starting material/needs only low amount of starting material, and (v) is able to reliable quantify in the range of 0.1-10% methylation and in the range of 90-99.9% methylation.

The HQM method can be performed as a real time PCR based method, as a blockcycler PCR based method in combination with suitable detection systems like, for example, but not limited to it, an agarose gel or a hybridisation platform (e.g. oligonucleotide array), MSP or Headloop.

The invention claimed is:

1. A method for methylation analysis of a nucleic acid, comprising
providing a double stranded nucleic acid,
converting said nucleic acid in such a way that 5-methylcytosine remains unchanged, while unmethylated cytosine is converted to uracil or to another base that is distinguished by cytosine in its base-pairing behavior, said reaction leading to two different converted nucleic acid strands that are no longer complementary to each other,
analyzing both of the converted nucleic acid strands, wherein one of the two strands is analyzed in a methylation specific manner and the other of the two strands is analyzed in a non-methylation specific manner, wherein
(i) the methylation-specific manner comprises the analysis of the presence or absence of methylation of one or more cytosines; and
(ii) the non-methylation specific manner comprises the analysis of the copy number, deletion or amplification of one or more adjacent nucleotides in a corresponding, overlapping, adjacent or different section of the second strand or an analysis of SNP.

2. A method of claim 1, wherein the converting of nucleic acid comprises a chemical reagent, bisulfite, an enzyme, or a cytidine-deaminase.

3. A method of claim 1, wherein analyzing both of the converted nucleic acid strands comprises the analysis of corresponding, overlapping, adjacent or different sections of the strands of the originally provided nucleic acid.

4. A method of claim 1, wherein analyzing both of the converted nucleic acid strands comprises (a) the quantification of methylation or non-methylation of one or more CpG positions; and (b) the quantification of converted nucleic acid; or the quantification of unconverted nucleic acids.

5. A method of claim 1, wherein analyzing both of the converted nucleic acid strands comprises at least one method selected from the group consisting of amplification method, PCR method, isothermal amplification method, NASBA method, LCR method, methylation specific amplification method, MSP (Methylation Specific PCR) method, nested MSP method, HeavyMethyl™ method, methylation specific detection method, bisulfite sequencing method, detection by means of microarrays, detection by means of oligonucleotide microarrays, detection by means of restriction enzymes, simultaneous methylation specific amplification and detection method, real-time PCR, HeavyMethyl™ real time PCR method, MSP MethyLight™ method, MethyLightTM method, MethyLight™ A1go™ method, QM method, Headloop MethyLight™ method, HeavyMethyl™ MethyLight™ method, HeavyMethyl™ Scorpion™ method, MSP Scorpion™ method, Headloop Scorpion™ method, methylation sensitive primer extension, and Ms-SNuPE (Methylation-sensitive Single Nucleotide Primer Extension) method.

6. A method according to claim 1, wherein genomic DNA is analyzed by real time PCR.

7. A method of claim 1, wherein the methylation specific manner comprises a real time quantitative methylation method and wherein the non-methylation specific manner comprises a real time PCR method.

* * * * *

SEQUENCE LISTING

<160> NUMBER OF SEQ ID NOS: 11

<210> SEQ ID NO 1
<211> LENGTH: 25
<212> TYPE: DNA
<213> ORGANISM: Artificial Sequence
<220> FEATURE:
<223> OTHER INFORMATION: forward primer A

<400> SEQUENCE: 1
aaaaaaaaaa aactcctcta catac        25

<210> SEQ ID NO 2
<211> LENGTH: 24
<212> TYPE: DNA
<213> ORGANISM: Artificial Sequence
<220> FEATURE:
<223> OTHER INFORMATION: reverse primer A

<400> SEQUENCE: 2
ggttattgtt tgggttaata aatg        24

<210> SEQ ID NO 3
<211> LENGTH: 38
<212> TYPE: DNA
<213> ORGANISM: Artificial Sequence
<220> FEATURE:
<223> OTHER INFORMATION: blocker A

<400> SEQUENCE: 3
acatacacca caaataaatt accaaaaaca tcaaccaa        38

<210> SEQ ID NO 4
<211> LENGTH: 19
<212> TYPE: DNA
<213> ORGANISM: Artificial Sequence
<220> FEATURE:
<223> OTHER INFORMATION: probe A

<400> SEQUENCE: 4
ttcggacgtc gttgttcgg        19

<210> SEQ ID NO 5
<211> LENGTH: 25
<212> TYPE: DNA

-continued

```
<213> ORGANISM: Artificial Sequence
<220> FEATURE:
<223> OTHER INFORMATION: forward primer B

<400> SEQUENCE: 5
gaaagagaaa ggttttttg tatac                                          25

<210> SEQ ID NO 6
<211> LENGTH: 24
<212> TYPE: DNA
<213> ORGANISM: Artificial Sequence
<220> FEATURE:
<223> OTHER INFORMATION: reverse primer B

<400> SEQUENCE: 6
aatcactacc taaaccaaca aata                                          24

<210> SEQ ID NO 7
<211> LENGTH: 26
<212> TYPE: DNA
<213> ORGANISM: Artificial Sequence
<220> FEATURE:
<223> OTHER INFORMATION: blocker B

<400> SEQUENCE: 7
tgtatacgtc gcgggtgggt tgtcgg                                        26

<210> SEQ ID NO 8
<211> LENGTH: 22
<212> TYPE: DNA
<213> ORGANISM: Artificial Sequence
<220> FEATURE:
<223> OTHER INFORMATION: probe B

<400> SEQUENCE: 8
cttcccaaac accactaccc aa                                            22

<210> SEQ ID NO 9
<211> LENGTH: 22
<212> TYPE: DNA
<213> ORGANISM: Artificial Sequence
<220> FEATURE:
<223> OTHER INFORMATION: probe C

<400> SEQUENCE: 9
tcaaccaaac aacaacatcc aa                                            22

<210> SEQ ID NO 10
<211> LENGTH: 113
<212> TYPE: DNA
<213> ORGANISM: Artificial Sequence
<220> FEATURE:
<223> OTHER INFORMATION: TMEFF 2 genomic region after bisulfite
      conversion (upper strand)

<400> SEQUENCE: 10
gaaagagaaa ggttttttg tatatgttgt gggtgggttg ttgggagtat tggttgggta    60
gtggtgtttg ggaaggggag agtgggtttt atttgttggt ttaggtagtg att         113

<210> SEQ ID NO 11
<211> LENGTH: 113
<212> TYPE: DNA
<213> ORGANISM: Artificial Sequence
<220> FEATURE:
<223> OTHER INFORMATION: TMEFF 2 genomic region after bisulfite
      conversion (lower strand):
```

```
<400> SEQUENCE: 11
aaaaaaaaaa aactcctcta catacgccgc gaataaatta ccgaaaacat cgaccgaaca        60
acgacgtccg aaaaaaaaaa aacgaactcc atttattaac ccaaacaata acc             113
```